(12) United States Patent
Zakrzewski et al.

(10) Patent No.: US 10,350,243 B2
(45) Date of Patent: Jul. 16, 2019

(54) METHODS FOR OFF-THE-SHELF-TUMOR IMMUNOTHERAPY USING ALLOGENEIC T-CELL PRECURSORS

(71) Applicant: Memorial Sloan-Kettering Cancer Center, New York, NY (US)

(72) Inventors: Johannes L. Zakrzewski, New York, NY (US); Marcel R. m. Van Den Brink, New York, NY (US); Michel Sadelain, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 15/048,550

(22) Filed: Feb. 19, 2016

(65) Prior Publication Data

US 2017/0049818 A1 Feb. 23, 2017

Related U.S. Application Data

(62) Division of application No. 12/865,592, filed as application No. PCT/US2009/000606 on Jan. 30, 2009.

(60) Provisional application No. 61/006,759, filed on Jan. 30, 2008.

(51) Int. Cl.
| | |
|---|---|
| *A61K 35/26* | (2015.01) |
| *A61K 35/28* | (2015.01) |
| *A61K 35/17* | (2015.01) |
| *C07K 14/705* | (2006.01) |

(52) U.S. Cl.
CPC ............ *A61K 35/17* (2013.01); *C07K 14/705* (2013.01)

(58) Field of Classification Search
None
See application file for complete search history.

(56) References Cited

U.S. PATENT DOCUMENTS

| | | | |
|---|---|---|---|
| 5,830,755 A | * 11/1998 | Nishimura | ....... C07K 14/70535 424/93.2 |
| 6,544,506 B2 | 4/2003 | Reisner | |
| 2004/0067583 A1 | 4/2004 | Bernstein et al. | |
| 2004/0171148 A1 | 9/2004 | Schmitt et al. | |
| 2007/0154473 A1 | 7/2007 | Super et al. | |
| 2007/0292417 A1 | 12/2007 | Siemionow | |

FOREIGN PATENT DOCUMENTS

WO     WO 9211355     * 7/1992

OTHER PUBLICATIONS

Seinstra et al ( Human gene Therapy, 2007, v.18 p. 1064.*
Finer et al., ( Experiment Bone Marrow Transplant, 1993, v.82 pp. 217A.*
U.S. Appl. No. 12/865,592 (U.S. Pat. No. 2011/0052554), filed Nov. 22, 2010 (dated Mar. 3, 2011).
U.S. Appl. No. 12/865,592, dated Feb. 23, 2016 Applicant Initiated Interview Summary.
U.S. Appl. No. 12/865,592, dated Feb. 22, 2016 Notice of Appeal Filed.
U.S. Appl. No. 12/865,592, dated Aug. 20, 2015 Final Office Action.
U.S. Appl. No. 12/865,592, dated Apr. 15, 2015 Amendment and Request for Continued Examination (RCE).
U.S. Appl. No. 12/865,592, dated Oct. 16, 2014 Final Office Action.
U.S. Appl. No. 12/865,592, dated Sep. 15, 2014 Response to Non-Final Office Action.
U.S. Appl. No. 12/865,592, dated Apr. 16, 2014 Non-Final Office Action.
U.S. Appl. No. 12/865,592, dated Jul. 19, 2013 Request for Continued Examination (RCE).
U.S. Appl. No. 12/865,592, dated May 28, 2013 Advisory Action.
U.S. Appl. No. 12/865,592, dated May 21, 2013 Amendment and Request for Continued Examination (RCE).
U.S. Appl. No. 12/865,592, dated Apr. 15, 2013 Applicant Initiated Interview Summary.
U.S. Appl. No. 12/865,592, dated Feb. 22, 2013 Final Office Action.
U.S. Appl. No. 12/865,592, dated Jan. 15, 2013 Response to Non-Final Office Action.
U.S. Appl. No. 12/865,592, dated Oct. 23, 2012 Non-Final Office Action.
U.S. Appl. No. 12/865,592, dated Aug. 30, 2012 Response to Requirement Restriction.
U.S. Appl. No. 12/865,592, dated Aug. 3, 2012 Requirement Restriction Filed.
Bachar-Lustig, E., et al., "Induction of Donor-Type Chimerism and Transplantation Tolerance Across Major Histocompatibility Barriers in Sublethally Irradiated Mice by Sca-1 +Lin-Bone Marrow Progenitor Cells: Synergism With Non-Alloreactive (Host x Donor)F1 T Cells", www.bloodjournal.org., 94, pp. 3212-3221, 1999.
Feldman et al., "Anti-TNFα Therapy is Useful in Rheumatoid Arthritis and Crohn's Disease: Analysis of the Mechanism of Action Predicts Utility in Other Diseases," Transplant. Proc. 1998, 30, 4126-4127.
Gade, T. P. F., et al., "Targeted Elimination of Prostate Cancer by Genetically Directed Human T Lymphocytes", American Association for Cancer Research, 65(9),9080-9088, Oct. 1, 2005.
Laurence et al., "TH-17 differentiation: of mice and men," Nature Immunol, 2007, v. 8 No. 9, pp. 903-905.
Mestas et al., "Of Mice and Not Men: Differences between Mouse and Human Immunology," J. of Immunology, 2004, 172, pp. 2731-238.

(Continued)

*Primary Examiner* — Michail A Belyavskyi
(74) *Attorney, Agent, or Firm* — Baker Botts L.L.P.

(57) ABSTRACT

The inventive subject matter relates to methods for treating a T-cell deficiency in a subject in need thereof, comprising administering to said subject a T-cell precursor isolated from an allogeneic donor, provided that said allogeneic donor is not MHC-matched to said subject. The inventive methods can be further enhanced by genetic engineering for targeted immunotherapy.

10 Claims, 27 Drawing Sheets

(56) References Cited

OTHER PUBLICATIONS

Tefveson et al., "New Immunosuppressants: Testing and Development in Animal Models and the Clinic: with Special Reference to DSG," Immun. Reviews 1993, No. 136, pp. 101-107.
Zakrzewski, J. L., et al., "Adoptive transfer of T-cell precursors enhances T-cell reconstitution after allogeneic hematopoietic stem cell transplantation", Nature Medicine, vol. 12, No. 9, pp. 1039-1047, Sep. 2006.
U.S. Appl. No. 12/865,592, dated Jun. 7, 2018 Notice of Allowance.
U.S. Appl. No. 12/865,592, dated May 15, 2018 Notice of Allowance.
U.S. Appl. No. 12/865,592, dated Apr. 16, 2018 Notice of Allowance.
U.S. Appl. No. 12/865,592, dated Apr. 16, 2018 Applicant Initiated Interview Summary.
U.S. Appl. No. 12/865,592, dated Apr. 10, 2018 Request for Continued Examination (RCE).
U.S. Appl. No. 12/865,592, dated Feb. 13, 2018 Notice of Appeal Filed.
U.S. Appl. No. 12/865,592, dated Sep. 13, 2017 Final Office Action.
U.S. Appl. No. 12/865,592, dated Apr. 21, 2017 Amendment and Request for Continued Examination (RCE).
U.S. Appl. No. 12/865,592, dated Dec. 21, 2016 Final Office Action.
U.S. Appl. No. 12/865,592, dated Jun. 24, 2016 Amendment and Request for Continued Examination (RCE).
Abe et al., "Characterization of a New Minor Lymphocyte Stimulatory System. I. Cluster of Self Antigens Recognized by "I-E-Reactive" V$\beta$s, V$\beta$5, V$\beta$11, and V$\beta$12 T Cell Receptors for Antigen," J. Immunology 147(3):739-749 (1991).
Acha-Orbea et al., "Superantigens of Mouse Mammary Tumor Virus," Annu. Rev. Immunol. 13:459-486 (1995).
Anderson et al., "Lymphostromal Interactions in Thymic Development and Function," Nat Rev Immunol 1:31-40 (2001).
Appelbaum, F.R., "Haematopoietic cell transplantation as immunotherapy," Nature 411:385-389 (2001).
Bill et al., "The MHC Molecule I-E is Necessary but not Sufficient for the Clonal Deletion of V$\beta$11-Bearing T Cells," J. Exp. Med. 169:1405-1419 (1989).
Bix et al., "Inefficient positive selection of T cells directed by haematopoietic cells," Nature 359:330-333 (1992).
Bousso et al., "Dynamics of Thymocyte-Stromal Cell Interactions Visualized by Two-Photon Microscopy" Science 296:1876-1880 (2002).
Brentjens et al., "Eradication of systemic B-cell tumors by genetically targeted human T lymphocytes co-stimulated by CD80 and interleukin-15," Nat Med 9(3):279-286 (2003).
Chinen et al., "Advances in basic and clinical immunology," J. Allergy Clin Immunol 118:489-495 (2006).
Cohen, "Benign and Malignant Epstein-Barr Virus-Associated B-cell Lymphoproliferative Diseases," Semin Hematol 40(2):116-123 (2003).
Cooke et al., "An Experimental Model of Idiopathic Pneumonia Syndrome after Bone Marrow Transplantation: I. The Roles of Minor H Antigens and Endotoxin," Blood 8(8):3230-3239 (1996).
Dallas et al., "Enhanced T-cell reconstitution by hematopoietic progenitors expanded ex vivo using the Notch ligand Delta 1," Blood 109:3579-3587 (2007).
De Smedt et al., "Human bone marrow CD34+ progenitor cells mature to T cells on OP9-DL1 stromal cell line without thymus microenvironment," Blood Cells, Molecules, and Diseases 33:227-232 (2004).
Dik et al., "New Insights on human T cell development by quantitative T cell receptor gene rearrangement studies and gene expression profiling" JEM (2005);201(11):1715-12723.
Ernst et al., "Bone Marrow-derived Cells Fail to Induce Positive Selection in Thymus Reaggregation Cultures," J. Exp. Med. 183:1235-1240 (1996).
Fischer et al., "Naturally Occurring Primary Deficiencies of the Immune System," Annu. Rev. Immunol. 15:93-124 (1997).
Germain "T-Cell Development and the Cd4—Cd8 Lineage Decision" Nat Rev Immunol. (2002);2(5):309-22.
Gordan et al., "Correlation of early lymphocyte recovery and progression-free survival after autologous stem-cell transplant in patients with Hodgkin's and non-Hodgkin's Lymphoma," Bone Marrow Transplantation 31:1009-1013 (2003).
Gottschalk et al., "Adoptive immunotherapy for EBV-associated malignancies," Leuk & Lymphoma 46(1):1-10 (2005).
Gottschalk et al., "Treatment of Epstein-Barr Virus-Associated Malignancies with Specific T Cells," Adv Cancer Res 84:175-201 (2002).
Greiner et al., "Expression of tumor-associated antigens in acute myeloid leukemia: Implications for specific immunotherapeutic approaches," Blood 108:4109-4117 (2006).
Grunebaum et al., "Human T Cell Immunodeficiency: When Signal Transduction Goes Wrong," Immunol Res 34(1-2):117-125 (2006).
Heinzel et al., "Bone Marrow-Derived Hemopoietic Precursors Commit to the T Cell Lineage Only after Arrival in the Thymic Microenvironment" J Immunology (2007);178:858-868.
Heslop et al., "Donor T cells to Treat EBV-Associated Lymphoma," N Engl J Med 331(10):679-680 (1994).
Hill et al., "Total Body Irradiation and Acute Graft-Versus-Host Disease: The Role of Gastrointestinal Damage and Inflammatory Cytokines," Blood 90(8):3204-3213 (1997).
Joao et al., "Early lymphocyte recovery after autologous stem cell transplantation predicts superior survival in mantle-cell lymphoma," Bone Marrow Transplant 37:865-871 (2006).
June, "Adoptive T cell therapy for cancer in the clinic," J Clin Invest 117(6):1466-1476 (2007).
Kessels et al., "Immunotherapy through TCR gene transfer," Nat Immunol 2(10):957-961 (2001).
Kolb et al., "Graft-Versus-Leukemia Effect of Donor Lymphocyte Transfusions in Marrow Grafted Patients," Blood 86(5):2041-2050 (1995).
La Motte-Mohs et al., "Induction of T-cell development from human cord blood hematopoietic stem cells by Delta-like 1 in vitro," Blood 105:1431-1439 (2005).
Leemhuis et al., "A phase I Trial of Autologous Cytokine-Induced Killer Cells for the Treatment of Relapsed Hodgkin Disease and Non-Hodgkin Lymphoma," Biol Blood Marrow Transplantation 11:181-187 (2005).
Lehrnbecher et al., "Therapy-Induced Alterations in Host Defense in Children Receiving Therapy for Cancer," J Pediatr Hematol/Oncol 19(5):399-417 (1997).
Liggins et al., "Identification of Lymphoma-Associated Antigens Using SEREX," from Methods in Molecular Medicine, vol. 115: Lymphoma: Methods and Protocols, Edited by T. Illidge and P.W.M. Johnson, pp. 109-128 (2005).
Luznik et al., "Successful therapy of metastatic cancer using tumor vaccines in mixed allogeneic bone marrow chimeras," Blood 101(4):1645-1652 (2003).
Mackall et al., "Thymic aging and T-cell regeneration," Immunol Rev 160:91-102 (1997).
May et al., "Therapeutic haemoglobin synthesis in $\beta$-thalassaemic mice expressing lentivirus-encoded human $\beta$-globin," Nature 406:82-86 (2000).
Morgan et al., "Cancer Regression in Patients After Transfer of Genetically Engineered Lymphocytes," Science 314:126-129 (2006).
Ohishi et al., "Delta-1 enhances marrow and thymus repopulating ability of human CD34(+) CD38(−) cord blood cells," J. Clin. Invest. 110:1165-1174 (2002).
Papapetrou et al., "Harnessing endogenous miR-181a to segregate transgenic antigen receptor expression in developing versus post-thymic T cells in murine hematopoietic chimeras," J Clin Invest, 119(1):157-168 (2009).
Petrie et al., "Zoned Out: Functional Mapping of Stromal Signaling Microenvironments in the Thymus" Annual Review of Immunology (2007);25: 649-679.
Porrata et al., "Early lymphocyte recovery is a predictive factor for prolonged survival after autologous hematopoietic stem cell transplantation for acute myelogenous leukemia," Leukemia 16:1311-1318 (2002).

(56) References Cited

OTHER PUBLICATIONS

Porrata et al., "Early lymphocyte recovery post-autologous haematopoietic stem cell transplantation is associated with better survival in Hodgkin's disease," Br J Haematol 117:629-633 (2002).
Porrata et al., "Early lymphocyte recovery predicts superior survival after autologous hematopoietic stem cell transplantation in multiple myeloma or non-Hodgkin lymphoma," Blood 98:579-585 (2001).
Porrata et al., "Prolonged survival associated with early lymphocyte recovery after autologous hematopoietic stem cell transplantation for patients with metastatic breast cancer," Bone Marrow Transplantation 28:865-871 (2001).
Rooney et al., "Infusion of Cytotoxic T Cells for the Prevention and Treatment of Epstein-Barr Virus-Induced Lymphoma in Allogeneic Transplant Recipients," Blood 92(5):1549-1555 (1998).
Rooney et al., "Use of gene-modified virus-specific T lymphocytes to control Epstein-Barr-virus-related lymphoproliferation," Lancet 345:9-13 (1995).
Sadelain et al., "Targeting Tumours with Genetically Enhanced T Lymphocytes," Nat Rev Cancer 3:35-45 (2003).
Schmitt et al., "Induction of T cell development and establishment of T cell competence from embryonic stem cells differentiated in vitro," Nat Immunology 5(4):410-417 (2004).
Schmitt et al., "Induction of T Cell Development from Hematopoietic Progenitor Cells by Delta-like-1 In Vitro," Immunity 17:749-756 (2002).
Shen et al., "T/NK Bipotent Progenitors in the Thymus Retain the Potential to Generate Dendritic Cells," J. Immunology 171:3401-3406 (2003).
Terwey et al., "CCR2 is required for CD8-induced graft-versus-host disease," Blood 106:3322-3330 (2005).
Vacchio et al., "Selective Decreases in T Cell Receptor Vβ Expression. Decreased Expression of Specific Vβ Families is Associated with Expression of Multiple MHC and Non-MHC Gene Products," J Exp Med 170:1335-1346 (1989).
Vardi et al., "Two-sample tests for growth curves under dependent right censoring," Biometrika 88(4):949-960 (2001).
Weerkamp et al., "Wnt signaling in the thymus is regulated by differential expression of intracellular signaling molecules" PNAS (2006);103(9):3322-3326.
Woodland et al., "Requirement for Cotolerogenic Gene Products in the Clonal Deletion of I-E Reactive T Cells," Science 247:964-967 (1990).
Wu et al., "Thymic Dendritic Cell Precursors: Relationship to the T Lymphocyte Lineage and Phenotype of the Dendritic Cell Progeny," J, Exp. Med. 184:903-911 (1996).
Yang et al., "Generation of functional antigen-specific T cells in defined genetic backgrounds by retrovirus-mediated expression of TCR cDNAs in hematopoietic precursor cells," PNAS USA 99(9):6204-6209 (2002).
Yarilin et al., "Late T cell deficiency in victims of the Chernobyl radiation accident: possible mechanisms of induction," Int. J. Radiat. Biol. 63(4):519-528 (1993).
Yotnda et al., "Cytotoxic T Cell Response Against the Chimeric p210 BCR-ABL Protein in Patients with Chronic Myelogenous Leukemia," J. Clin. Invest. 101(10):2290-2296 (1998).
Zhao et al., "Extrathymic Generation of Tumor-Specific T Cells from Genetically Engineered Human Hematopoietic Stem Cells via Notch Signaling," Cancer Res 67(6):2425-2429 (2007).

\* cited by examiner

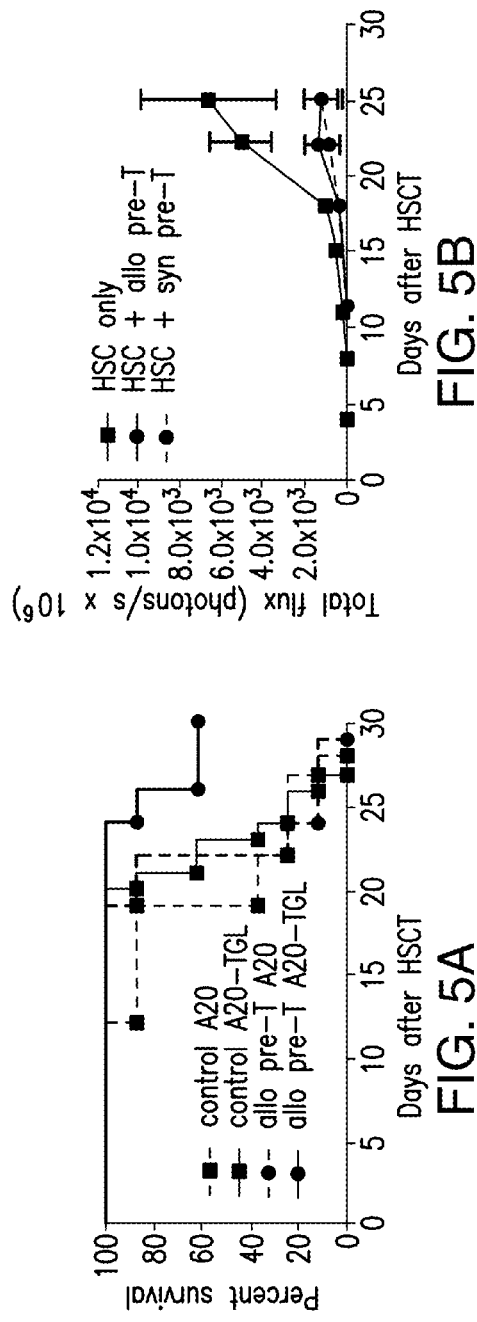
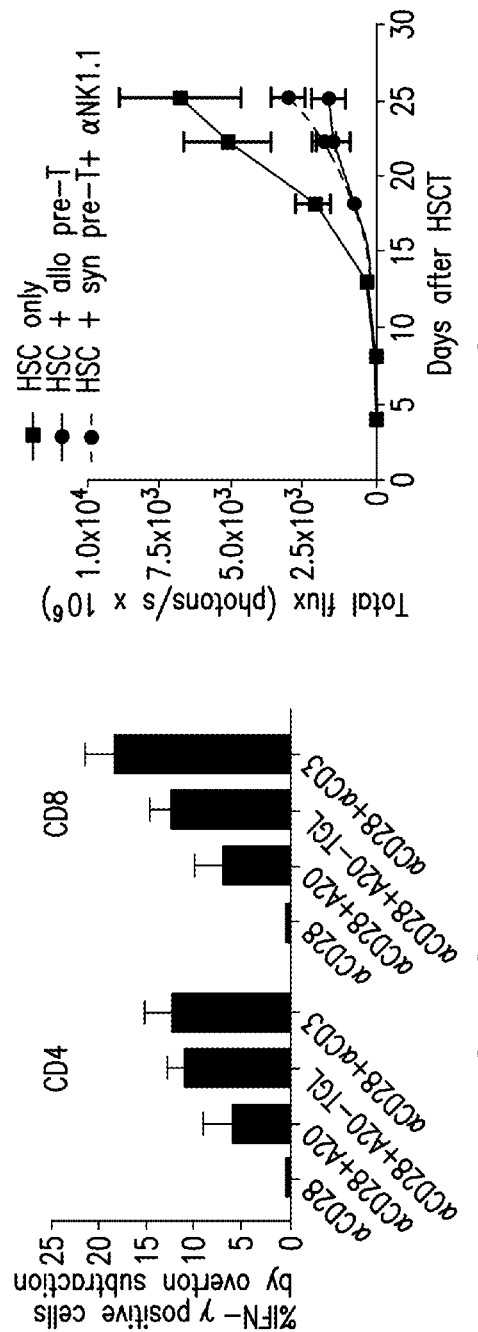
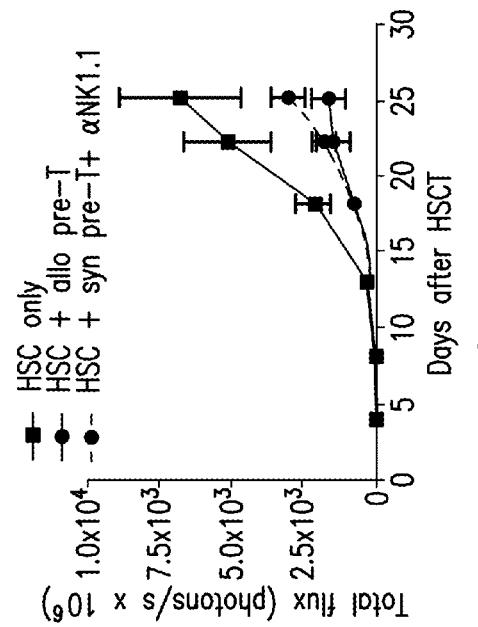

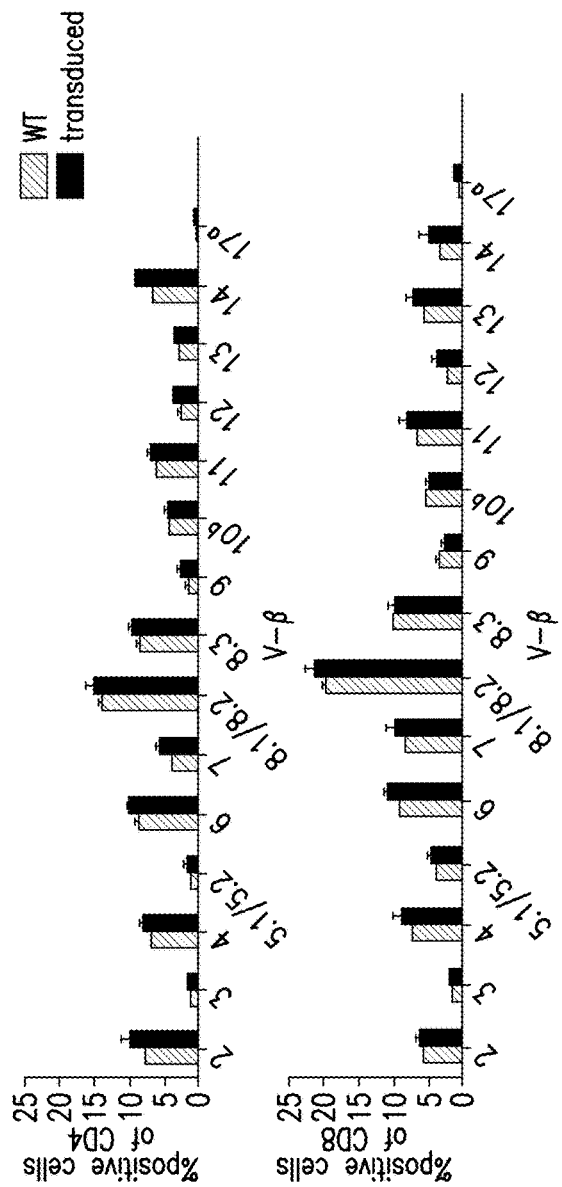
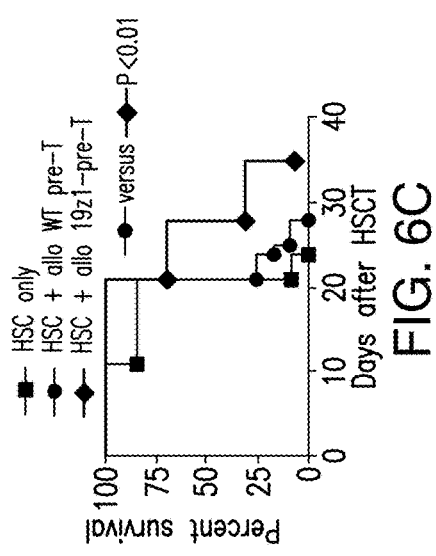
FIG. 6B
FIG. 6C

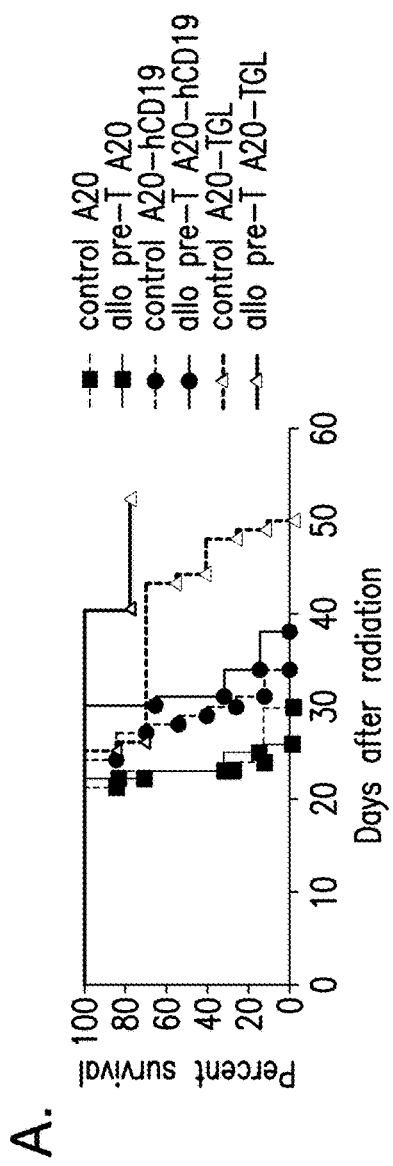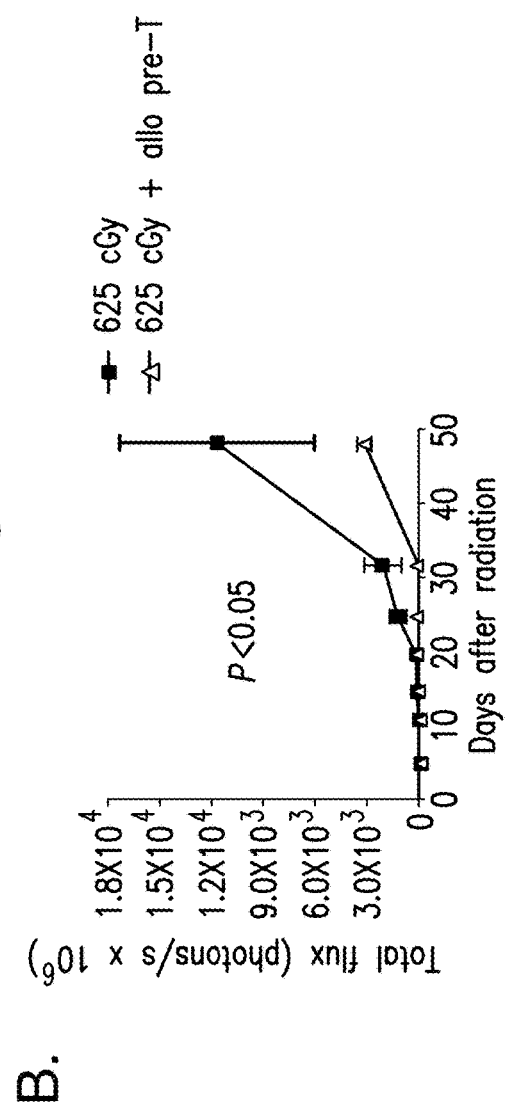
FIG. 11A
FIG. 11B

METHODS FOR OFF-THE-SHELF-TUMOR IMMUNOTHERAPY USING ALLOGENEIC T-CELL PRECURSORS

CROSS-REFERENCE TO RELATED APPLICATIONS

This application is a divisional of U.S. patent application Ser. No. 12/865,592, filed Nov. 22, 2010, which is a national phase application filed under 35 U.S.C. § 371 as a national stage of International Application Serial No PCT/US2009/000606, filed Jan. 30, 2009, which claims priority of U.S. Provisional Application Ser. No. 61/006,759, filed Jan. 30, 2008, the contents of each of which are incorporated by reference in their entirety, and to each of which priority is claimed.

GRANT INFORMATION

This invention was made with government support under grant numbers CA008748, CA107096, CA033049, CA040350, CA059350, CA083084 and GM007739 awarded by the National Institutes of Health. The government has certain rights in the invention.

BACKGROUND OF THE INVENTIVE SUBJECT MATTER

1. Field of Inventive Subject Matter

The inventive subject matter relates to novel methods for treating T-cell deficiencies using MHC-disparate T-cell precursors derived from universal donors in 'off-the-shelf' immunotherapy methods. For example, the inventive subject matter comprises treating individuals suffering from such conditions as T-cell-depletion following irradiation injury, T-cell-depletion following cytostatic therapy, and other diseases, disorders, and conditions resulting in T-cell-depletion. The inventive methods can be further enhanced by genetic engineering for targeted immunotherapy.

2. Background

Hematopoietic cell transplantation is the transplantation of blood stem cells derived from the bone marrow or blood of the donor, most often performed for people with diseases of the blood, bone marrow, or certain types of cancer.

Hematopoietic cell transplantation remains a risky procedure with many possible complications; it has heretofore been reserved for patients with life-threatening diseases.

T-cell deficiencies. T-cell deficiencies can occur in many physiological and pathophysiological settings. Thymic involution during aging is an important cause of thymic atrophy resulting in impaired T-cell function (see, for example, Mackall, C. L. & Gress, R. E. Thymic aging and T-cell regeneration. Immunol Rev 160, 91-102 (1997)). Various autoimmune disorders, genetic diseases, hematological malignancies, and infectious diseases are all associated with defective T-cell immunity (see, for example, Grunebaum, et al., Human T cell immunodeficiency: when signal transduction goes wrong. Immunol Res 35, 117-126 (2006); Fischer, et al., Naturally occurring primary deficiencies of the immune system. Annu Rev Immunol 15, 93-124 (1997); and Chinen, et al., Advances in basic and clinical immunology. J Allergy Clin Immunol 118, 489-495 (2006)).

Therapy-induced and unintentional exposures to cytostatic or cytotoxic agents, such as chemotherapeutics or gamma-irradiation, frequently cause transient or long-lasting T-cell deficiencies (see, for example, Lehrnbecher, et al., Therapy-induced alterations in host defense in children receiving therapy for cancer. J Pediatr Hematol Oncol 19, 399-417 (1997) and Yarilin, et al., Late T cell deficiency in victims of the Chernobyl radiation accident: possible mechanisms of induction. Int J Radiat Biol 63, 519-528 (1993)).

Hematopoietic stem cell transplantation. There are two primary types of hematopoietic stem cell transplantation ("HSCT"). Autologous HSCT involves isolation of hematopoietic stems cells (HSC) from the patient and storage of the harvested cells. The patient is then treated with high-dose chemotherapy with or without radiotherapy in the form of total body irradiation, to eradicate the patient's malignant cell population. This takes place at the cost of also eliminating the patient's bone marrow stem cells. In autologous HSCT, the patient's own stored stem cells are then returned to their body. Autologous transplants have the advantage of a lower risk of graft rejection and infection, since the recovery of immune function is rapid. The incidence of a patient experiencing graft-versus-host disease is close to none as the donor and recipient are the same individual.

Allogeneic HSCT involves two people, one is the (healthy) donor and one is the (patient) recipient. Allogeneic HSC donors must have a tissue (HLA) type that matches the recipient. Matching is performed on the basis of variability at three or more loci of the (HLA) gene, and a perfect match at these loci is preferred. Even if there is a good match at these critical alleles, the recipient will require immunosuppressive medications to mitigate graft-versus-host disease. Allogeneic transplant donors may be related (usually a closely HLA matched sibling) or unrelated (donor who is not related and found to have very close degree of HLA matching). Allogeneic transplants are also performed using umbilical cord blood as the source of stem cells.

Many recipients of HSCTs are leukemia patients who would benefit from treatment with high doses of chemotherapy or total body irradiation. Other conditions treated with stem cell transplants include sickle-cell disease, myelodysplastic syndrome, neuroblastoma, lymphoma, Ewing's Sarcoma, Desmoplastic small round cell tumor, Hodgkin's disease, and multiple myeloma. More recently non-myeloablative, or so-called "mini transplant," procedures have been developed that require smaller doses of preparative chemo and radiation.

HSCT is associated with a fairly high mortality in the recipient (10% or higher), which limits its use to conditions that are themselves life-threatening. Major causes of complications are veno-occlusive disease, mucositis, infection (sepsis) and graft-versus-host disease. HSCT is also associated with a particularly prolonged defect in T-cell function, yet the immunotherapeutic activity of an HSCT procedure is critical for its overall anti-tumor effect (see, for example, Appelbaum, Haematopoietic cell transplantation as immunotherapy. Nature 411, 385-389 (2001)). In the allogeneic setting, T-cells are primarily responsible for the negative effect of graft-versus-host disease (GVHD) and the therapeutic benefit of graft-versus-tumor (GVT) activity. Optimizing graft-versus-tumor activity while minimizing graft-versus-host disease is one of the major challenges in such transplants.

Graft-versus-host disease. Graft-versus-host disease (GVHD) is an inflammatory disease that is unique to allogeneic transplantation. It is an attack by transplanted leukocytes against the recipient's tissues. This can occur even if the donor and recipient are HLA-identical, because the immune system can still recognize other differences between tissues. It is aptly named graft-versus-host disease because bone marrow transplantation is the only transplant procedure in which the transplanted cells must accept the body rather than the body accepting the new cells. Acute graft-versus-host disease typically occurs in the first 3 months after transplantation and may involve the skin, intestine, or the liver. Corticosteroids such as prednisone are a standard treatment.

Chronic graft-versus-host disease may also develop after allogeneic transplant and is the major source of late complications. In addition to inflammation, chronic graft-versus-host disease may lead to the development of fibrosis, or scar tissue, similar to scleroderma or other autoimmune diseases and may cause functional disability, and the need for prolonged immunosuppressive therapy. Graft-versus-host disease is usually mediated by T cells when they react to foreign peptides presented on the MHC of the host. Removal of these T cells before donation can lessen the risk of this disease.

T-cell based therapy. T-cell based therapies such as donor leukocyte infusion or protocols involving ex vivo expansion and manipulation of T-cells in order to generate tumor or virus-specific cells have been used for many years as strategies to enhance immune reconstitution and anti-tumor activity following hematopoietic stem cell transplantation. However, these therapies are associated with a variety of problems including the following:

a. limited availability of suitable cells because T-cells have to be either autologous or MHC-matched allogeneic;
b. contamination with residual malignant T-cells when using autologous cells;
c. graft-versus-host disease when using allogeneic cells;
d. in vivo, cytokine administration is required during hematopoietic stem cell transplantation; and
e. adoptively transferred cells have a short life span.

Zakrzewski, et al., *Adoptive transfer of T-cell precursors enhances T-cell reconstitution after allogeneic hematopoietic stem cell transplantation*, Nat Med., 12(9):1039-(2006), is fairly indicative of the general understanding of skilled artisans in the relevant art, that the use of adoptive T-cell therapies requires co-administration of HSCs.

United States Patent Publication No. 2004/0067583 (Bernstein, et al.), requires either an autograft of T-cell precursors or an allograft of T-cell precursors which requires co-administration of immunosuppressives and co-administration of allogeneic HSCs, and fails to teach or suggest the use of CD4– CD8– double negative (DN) precursor cells.

United States Patent Publication No. 2004/0171148 (Schmitt, et al.), requires either an autograft of T-cell precursors or an allograft of T-cell precursors which requires co-administration immunosuppressives and co-administration of allogeneic HSCs.

Thus, the use of adoptive T-cell therapies is often limited by barriers imposed by MHC disparity. There is a long-felt and unmet need in the art to develop a way to address T-cell deficiencies without rejection, alloreactivity, and impaired antigen presentation, and to identify a universal donor strategy which does not require long term administration of immunosuppressives to graft recipients. The inventive subject matter provides methods which reduce or eliminate these problems, for the first time demonstrating that lymphoid precursor cells from a non-MHC-matched universal donor can be successfully transferred to any individual, irrespective of MHC disparities. Applicants have demonstrated that allogeneic T-cell precursors, when adoptively transferred to irradiated recipients, without syngeneic hematopoietic stem cells, develop into functional mature T-cells.

Surprisingly, Applicants have found that allogeneic T-cell precursors are effective when used alone for adoptive transfer across MHC barriers, even in the absence of allogeneic hematopoietic stem cells, and are able to overcome T-cell deficiencies such as injury resulting from exposure to radiation and diminished T-cell function. Further, in individuals undergoing cancer treatment and others with T-cell deficiencies, allogeneic T cell precursor transfer can improve anti-tumor activity in immunosuppressed recipients.

Thus, the inventive subject matter provides novel methods for therapy using adoptively transferred ex vivo generated allogeneic T-cell precursors that can develop into host-MHC restricted T-cells characterized by dual tolerance and selection of a functional TCR repertoire, even in a fully mismatched thymic epithelial MHC environment. Specifically, the primary advantages of utilizing T-cell precursors for immunotherapy are the following: (1) T-cell precursors do not have to be MHC matched, since graft-versus-host disease is not an issue; (2) the use of allogeneic precursors cells instead of autologous cells eliminates the risk of contamination with residual malignant autologous cells; and (3) the generation and storage of virtually unlimited quantities of precursor cells from universal donors for 'off-the-shelf' immunotherapy is thus achieved.

The inventive methods have these substantial logistic and technical advantages, and additionally facilitate the use of ex vivo manipulation protocols, in particular genetic engineering, to generate target-antigen-specific or otherwise enhanced designer cells. Adoptive transfer of MHC mismatched and genetically enhanced T-cell precursors therefore represents a novel, labor-saving, and cost-effective process for targeted 'off-the-shelf' immunotherapy for patients with a malignant disease or other T-cell deficiency.

SUMMARY OF THE INVENTIVE SUBJECT MATTER

Applicants have found, unexpectedly, that allogeneic T cell precursors can be transferred to any irradiated or otherwise T-cell-depleted individual, irrespective of MHC disparities, and give rise to host-MHC restricted and host tolerant allogeneic T-cells which are fully functional and span the full T-cell receptor repertoire. Transfer of allogeneic T cell precursors significantly improves survival and enhances anti-tumor activity in irradiated and other T-cell-depleted recipients. Applicants have also been able to successfully generate large numbers of such committed T-cell precursors from hematopoietic stem cells (HSCs), using a bone marrow-derived stromal cell line expressing the Notch ligand Delta-like 1.

In one embodiment of the inventive subject matter, Applicants have found that transfer of T-cell precursors transduced to express a chimeric receptor targeting human CD19 resulted in significant additional anti-tumor activity compared to T-cell precursors lacking the CD19 receptor, demonstrating the general feasibility of genetic engineering of these cells.

Applicants have shown that ex vivo-generated, MHC-disparate T-cell precursors from universal donors can be used in the inventive methods for 'off-the-shelf' immunotherapy, for example in treating individuals suffering from such conditions as T-cell-depletion following irradiation injury, T-cell-depletion following cytostatic therapy, and other disorders resulting in T-cell-depletion. These methods can be further enhanced by genetic engineering for targeted immunotherapy.

Thus, the inventive subject matter relates to a method for treating a T-cell deficiency in a subject in need thereof, comprising administering to said subject a T-cell precursor isolated from an allogeneic donor, wherein the MHC of said allogeneic donor is not matched to the MHC of said subject.

Further, the inventive subject matter relates to a method for treating a T-cell deficiency in a subject in need thereof, consisting essentially of administering to said subject a T-cell precursor cell isolated from an allogeneic donor, wherein the MHC of said allogeneic donor is not matched to the MHC of said subject.

BRIEF DESCRIPTION OF THE DRAWINGS

FIG. 5A is a graph which depicts graft-versus-tumor activity of allogeneic T-cell precursors against A20-TGL cells.

FIG. 5B is a graph which depicts post-transplant BLI for A20-TGL tumor cell recipients.

FIG. 5C is a bar graph which depicts post-transplant percent IFN-γ expression.

FIG. 5D is a graph which depicts post-transplant BLI in relation to depletion of NK cells.

FIG. 6E is a series of bar graphs which depict analysis of TCR-Vβ families on CD4+ and CD8+ cells.

FIG. 6C is a graph which depicts post-transplant percentage of T-cells expressing hCD19.

FIG. 11A is a graph which depicts survival of A20, A20-hCD19 or A20-TGL tumor cell-challenged recipients.

FIG. 11B is a graph which depicts BLI of A20, A20-hCD19 or A20-TGL tumor cell-challenged recipients.

DETAILED DESCRIPTION OF THE INVENTIVE SUBJECT MATTER

Definitions

Figure 1A:
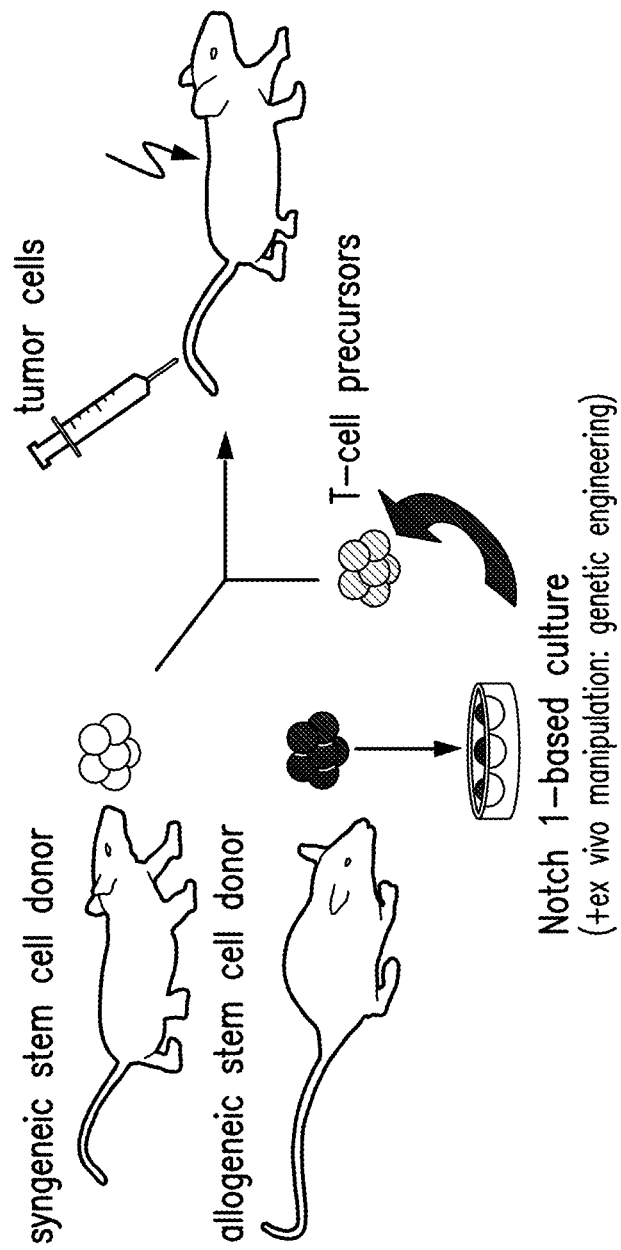
FIG. 1A is a drawing which depicts the experimental transplantation scheme utilized the Examples herein.

The term "enhancing" the biological activity, function, health, or condition of an organism refers to the process of augmenting, fortifying, strengthening, or improving.

The term "graft-versus-host disease" or "GVHD" as used herein refers to an inflammatory disease resulting from an attack by transplanted leukocytes against the tissues of the transplant recipient.

The term "graft versus tumor" or "GVT" as used herein refers to the beneficial aspect of the graft-versus-host phenomenon, in which a therapeutic immune reaction of the grafted donor lymphocytes, generally Natural Killer (NK) cells, against the diseased tissue of the graft recipient.

The term "co-administration" as used herein refers to the process of administering two or more active agents together during a single course of treatment, including pre-treatment administration and post-treatment administration.

The term "chimeric antigen receptor" or "CAR" as used herein refers to an engineered molecule, which when expressed by T cells, redirect the T cells to kill a target cell with a specificity dictated by the artificial receptor.

The term "MHC-matched" as used herein refers to the condition in which a graft donor has the same human leukocyte antigens (HLA) as the graft recipient. An exact match is preferred, and the use of a mismatched donor increases the risk of graft rejection or graft-versus-host disease.

The term "universal donor" as used herein refers to a T cell precursor donor of any genetic background, irrespective of MHC disparities the donor may have with a transplant recipient.

The term "immunosuppressive composition" as used herein refers to a composition administered in order to prevent rejection of an administered allograft. Applicants characterize cytostatic agents secondarily resulting in immunosuppression as cytostatic agents, not as immunosuppressive compositions within the scope of this definition.

The Inventive Methods for Treating T-Cell Deficiencies

The use of adoptive T-cell therapies is often limited by barriers imposed by MHC disparity, resulting in rejection, alloreactivity and impaired antigen presentation. This application shows, for the first time, the surprising finding that lymphoid precursor cells from a non-MHC-matched universal donor can be successfully transferred to any individual, irrespective of MHC disparities. Applicants have demonstrated that allogeneic T-cell precursors, when adoptively transferred to irradiated recipients, without syngeneic hematopoietic stem cells, develop into functional mature T-cells.

The inventive subject matter thus relates to a method for treating a T-cell deficiency in a subject in need thereof, comprising administering to said subject a T-cell precursor isolated from an allogeneic donor, wherein the MHC of said allogeneic donor is not matched to the MHC of said subject. In the context of the inventive subject matter, every potential donor is a universal donor because T-cell precursors of any genetic background can be used universally. This means that T cell precursors from any donor can be transferred to any person in need, irrespective of the MHC disparities which have limited such graft procedures in the past. MHC matching is not required since the degree of MHC disparity does not matter, and it is expected that anything from fully matched MHC to fully mismatched MHC works equally well.

In another aspect of the inventive subject matter, said T-cell precursor cell is selected from the group consisting of one or more $CD4^-CD8^-$ double negative precursor cell lineages, or a combination thereof.

In a preferred embodiment, said double negative precursor cell is selected from the group consisting of DN2 ($CD44^+CD25^+$), DN3 ($CD44^-CD25^+$), DN2/3, an equivalent human DN T cell precursor phenotype, or a combination thereof.

In a more preferred embodiment, said double negative precursor cell is derived from lineage $lin^-Sca-1^+c-kit^{hi}$ or a human equivalent CD34+ lineage.

Without being bound to a particular mechanism of action, Applicants believe that MHC restriction of these precursor T-cells is determined by host MHC molecules which are encountered during T-cell development. Because of the DC lineage potential of T-cell precursors up to the DN2/3 stage and as a consequence of APC chimerism, tolerance of the resulting T-cells is dual. A major advantage of T lineage committed precursor cells with limited DC capacity is their potential to reconstitute an immunosuppressed or T-cell-deficient host with host-MHC-restricted allogeneic T-cells, while preserving a predominantly host APC chimerism. Controlling the APC chimerism translates into host tolerant and functional TCR selection, averting graft-versus-host disease and promoting immunity.

Therefore, adoptive therapy with T-cell precursors allows for universal 'off-the-shelf' T-cell immunotherapy, which is currently impossible with ex vivo generated or manipulated mature T-cells. Applicants expect that, in one embodiment of the inventive subject matter, using T-cell precursor therapy, optionally in combination with prior cytostatic conditioning, will be effective as a tumor immunotherapy, as well as a countermeasure for lymphopenia due to radiation injury.

Figure 17:
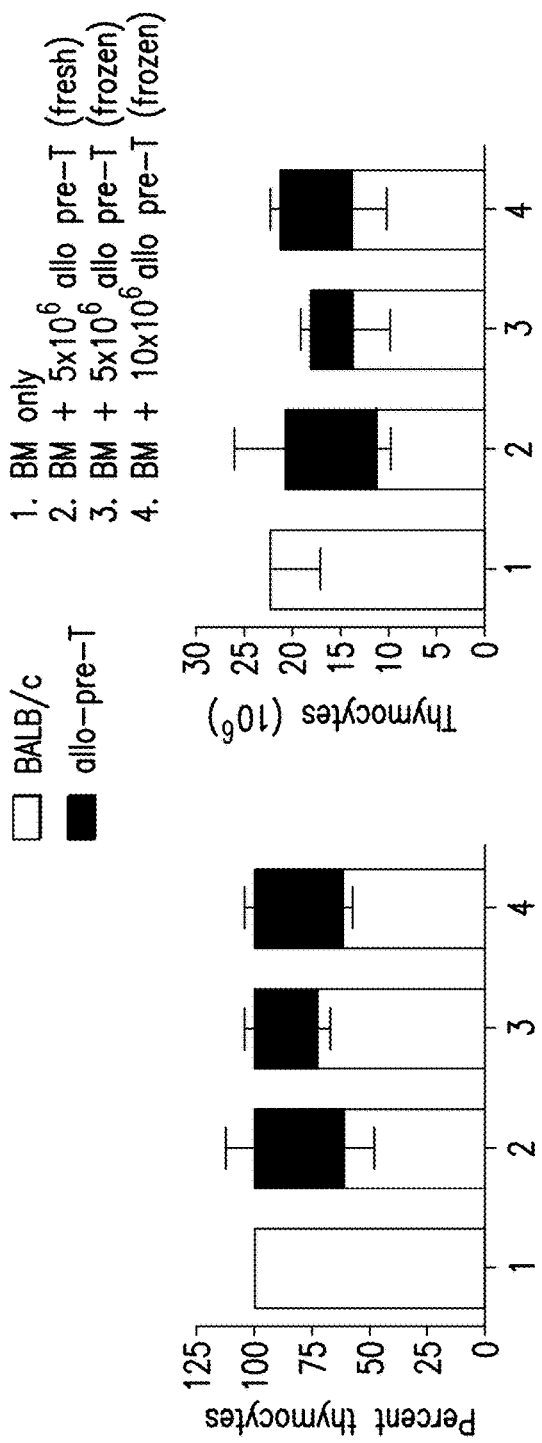
FIG. 17 is a series of graphs which depict donor and host progenies determined by total cellularity.

True 'off-the-shelf' therapy requires the ability to use cryopreserved cells, which is routinely done in the clinical setting with human hematopoietic progenitor cells. As shown in FIG. 17, it was found using Applicants' mouse model that adoptive transfer of cryopreserved allogeneic T-cell precursors to irradiated recipients results in stable thymic engraftment, demonstrating that cryopreserved T-cell precursors engraft in the thymus of irradiated recipients. Lethally irradiated BALB/c recipients were transplanted with BALB/c HSCs; control mice received HSCs only, the pre-T groups received additional C57BL/6 derived T-cell precursors (5×106 fresh or 5×106 cryopreserved or 10×106 cryopreserved cells). Thymi were harvested on day 14 after transplantation and donor and host progenies were determined by total cellularity and multicolor flow cytometric analysis using Ly9.1 and CD45-specific antibodies. Mean cell numbers+SEM are presented (n=4).

In a further aspect of the inventive subject matter, said method does not comprise co-administration of allogeneic hematopoietic stem cells; does not comprise co-administration of immunosuppressive compositions; or does not comprise co-administration of either hematopoietic stem cells or immunosuppressive compositions. In this regard, co-administration of hematopoietic stem cells is not required for the inventive method to be effective. However, some patients will receive high-dose chemotherapy followed by administration of autologous hematopoietic stem cells in combination with T cell precursors. However, these stem cells are given to prevent bone marrow failure after high dose chemotherapy, but they are not required for T cell precursor administration to be effective. The key distinction in this regard is that adoptive immunotherapy with allogeneic T cell precursors is always done in the absence of allogeneic hematopoietic stem cells.

Further, the inventive methods do not comprise co- or post-administration of immunosuppressive compositions in any sense. The inventive methods are effective in individuals that (a) do not reject the administered allogeneic T cell precursors and (b) receive some form of thymic conditioning, which is likely to be targeted mediastinal irradiation or total body irradiation, in order to allow thymic engraftment of the administered precursor cells. It may also be necessary to administer additional agents such as Interleukin 7 (IL-7) or antithymocyte globuline (ATG) to T cell precursor recipients to promote survival and enhance thymic engraftment of T cell precursors.

In the exemplary context of cancer patients, it is expected that prior to administration of precursor cells, potential recipients are treated with cytostatic agents. Cytostatic agents have a secondary effect resulting in immunosuppression, but are not immunosuppressive compositions within the meaning of the present claims. It is expected that additional immunosuppressive compositions to prevent rejection of administered allogeneic T cell precursors will not be required.

However, in some cases such as patients that do not receive total body irradiation or targeted mediastinal irradiation as part of their pre-treatment, it may be necessary to administer some form of thymic conditioning for the purpose of preparing the patient for T cell precursor administration. Such thymic condition will most likely comprise targeted thymic irradiation in combination with administration of IL-7, ATG or other agents that enhance the viability and thymic engraftment capacity of transferred T cell precursors.

Further, genetic engineering is a powerful preferred process for designing and producing tumor-associated antigen-specific cells. Preferred potential targets for transgenic receptors include, but are not limited to:
  a. immunogenic tumor proteins (see, e.g., Yotnda, et al., Cytotoxic T cell response against the chimeric p210 BCR-ABL protein in patients with chronic myelogenous leukemia. J Clin Invest 101, 2290-2296 (1998); Liggins, et al., Identification of lymphoma-associated antigens using SEREX. Methods Mol Med 115, 109-128 (2005); and Greiner, et al., Expression of tumor-associated antigens in acute myeloid leukemia: Implications for specific immunotherapeutic approach. Blood 108, 4109-4117 (2006))
  b. viral antigens in virus-associated cancers such as EBV-related lymphoma or lymphoproliferative disease (Gottschalk, et al., Adoptive immunotherapy for EBV-associated malignancies. Leuk Lymphoma 46, 1-10 (2005); Rooney, et al., Use of gene-modified virus-specific T lymphocytes to control Epstein-Barr-virus-related lymphoproliferation, Lancet 345, 9-13 (1995); and Cohen, J. I., Benign and malignant Epstein-Barr virus-associated B-cell lymphoproliferative diseases, Semin Hematol 40, 116-123 (2003)).

Thus, in an alternate aspect of the inventive subject matter, said non-MHC-matched T-cell precursor additionally comprises a nucleic acid sequence which codes for a chimeric antigen receptor which is capable of expression in said T-cell precursor.

In yet another aspect of the inventive subject matter, said non-MHC-matched T-cell precursor expresses a chimeric antigen receptor which is specific for an antigen of a target cancer cell.

In a preferred embodiment, said chimeric antigen receptor expresses an anti-CD19 protein.

In a more preferred embodiment, said chimeric antigen receptor is 19z1.

In another preferred embodiment, said non-MHC-matched T-cell precursor cell expresses one or more proteins selected from the group consisting of costimulatory molecules CD26, CD28, CD40, CD80, CD86, CD134, CD154, and combinations thereof.

In a further aspect of the inventive subject matter, said T-cell deficiency is selected from the group consisting of acute lymphoblastic leukemia, acute lymphocytic leukemia, acute myelogenous leukemia, aplastic anemia, chronic myelogenous leukemia, desmoplastic small round cell tumor, Ewing's sarcoma, Hodgkin's disease, multiple myeloma, myelodysplasia, Non-Hodgkin's lymphoma, paroxysmal nocturnal hemoglobinuria, radiation poisoning, chronic lymphocytic leukemia, AL amyloidosis, essential thrombocytosis, polycythemia vera, severe aplastic anemia, neuroblastoma, breast tumors, ovarian tumors, renal cell carcinoma, autoimmune disorders, such as systemic sclerosis, osteopetrosis, inherited metabolic disorders, juvenile chronic arthritis, adrenoleukodystrophy, amegakaryocytic thrombocytopenia, sickle cell disease, severe congenital immunodeficiency, Griscelli syndrome type 11, Hurler syndrome, Kostmann syndrome, Krabbe disease, metachromatic leukodystrophy, thalassemia, hemophagocytic lymphohistiocytosis, and Wiskott-Aldrich syndrome.

Finally, the inventive subject matter relates to a method for treating a T-cell deficiency in a subject in need thereof, consisting essentially of administering to said subject a T-cell precursor cell isolated from an allogeneic donor, wherein the MHC of said allogeneic donor is not matched to the MHC of said subject.

While hematopoietic stem cells have been transduced with TCR genes to obtain tumor-specific T-cells, such cells are usually quiescent, which makes them more difficult to transduce than proliferating cells such as early T-cell precursors, in particular DN1 cells. An important issue with engineering mature T-cells to express antigen-specific receptors is the ability to avoid or limit generating potentially harmful novel receptor specificities as a consequence of combining transgenic receptor and endogenous TCR chains. This scenario is of no concern when engineering T-cell precursors such as DN1 cells, since these cells have not yet selected a TCR and are expected to develop an appropriate TCR or be negatively selected out of the T-cell pool. Indeed, the main additional benefit of this approach is the ability to generate antigen-specific T-cell precursors that can be positively selected and are not subject to negative selection.

Donor T-cell precursors can be used without genetic modification, for example in treating lethally irradiated or seriously immunocompromised individuals. However, in merely immunodeficient individuals, genetically engineered T-cell precursors may be less likely to produce adverse side effects and are therefore preferred. In genetically engineering T-cell precursors, the goal of avoiding negative selection can be accomplished by transferring genes encoding for chimeric antigen receptors (CARs) instead of TCRs, allowing endogenous TCR expression and resulting in an intact, natural positive selection process for transgenic cells. The risk of clonal deletion can be reduced by targeting antigens that are distinct from self-antigens so that autoreactivity, if any, displayed by the antigen receptor is below the threshold that induces negative selection.

Since the mechanism of negative selection is very sensitive, optional additional strategies to better overcome this technical limitation can be utilized. Such techniques ensure optimal functionality while avoiding unwanted adverse effects of engineered cells (see, e.g. Brentjens, et al., Eradication of systemic B-cell tumors by genetically targeted human T lymphocytes co-stimulated by CD80 and interleukin-15. Nat Med 9, 279-286 (2003) and June, C. H., Adoptive T cell therapy for cancer in the clinic, J Clin Invest 117, 1466-1476 (2007)). Optional techniques include, but are not limited to:
  a. using promoters that allow temporal control of transgene expression, producing conditional expression or even better, maturation-dependent expression (see, e.g., Papapetrou E P, Kovalovsky D, Beloeil L, Sant'angelo D, Sadelain M, Harnessing endogenous miR-181a to segregate transgenic antigen receptor expression in developing versus post-thymic T cells in murine hematopoietic chimeras. J Clin Invest, 157-168 (2009));
  b. employing suicide switches as a safety feature;
  c. employing costimulatory signals to prevent T-cell anergy and apoptosis.

In particular, Applicants' have found that transducing T-cell precursors to express a chimeric antigen receptor targeting human CD19 resulted in excellent transduction efficiency and the in vivo generation of high numbers of appropriately selected T-cells expressing the chimeric antigen receptor, which were capable of significant anti-tumor activity without any undesirable autoreactivity or alloreactivity.

Thus, Applicants have demonstrated that adoptively transferred ex vivo generated allogeneic T-cell precursors can develop into host-MHC restricted T-cells characterized by dual tolerance and selection of a functional TCR repertoire, even in a fully mismatched thymic epithelial MHC environment. Specifically, the primary advantages of utilizing T-cell precursors for immunotherapy are the following: (1)

T-cell precursors do not have to be MHC matched, since graft-versus-host disease is not an issue; (2) the use of allogeneic precursors cells instead of autologous cells eliminates the risk of contamination with residual malignant autologous cells; and (3) the generation and storage of virtually unlimited quantities of precursor cells from universal donors for 'off-the-shelf' immunotherapy is thus achieved.

The inventive methods have these substantial logistic and technical advantages, and additionally facilitate the use of ex vivo manipulation protocols, in particular genetic engineering, to generate target-antigen-specific or otherwise enhanced designer cells. Adoptive transfer of MHC mismatched and genetically enhanced T-cell precursors therefore represents a novel, labor-saving, and cost-effective process for targeted 'off-the-shelf' immunotherapy for patients with a malignant disease or other T-cell deficiency. The fact that T cell precursors do not have to be MHC-tested and can simply be used like a drug is one of the features and advantages that makes this approach particularly attractive.

TABLE 1

Conditions treatable with T-cell precursor transplantation

Acquired

Acute lymphoblastic leukemia
Acute lymphocytic leukemia
Acute myelogenous leukemia
Aplastic anemia
Chronic myelogenous leukemia (accelerated phase or blast crisis)
Desmoplastic small round cell tumor
Ewing's sarcoma
Hodgkin's disease
Multiple myeloma (Kahler's disease)
Myelodysplasia
Non-Hodgkin's lymphoma
Paroxysmal nocturnal hemoglobinuria (PNH; severe aplasia)
Radiation poisoning
chronic lymphocytic leukemia
AL amyloidosis
Essential thrombocytosis
Polycythemia vera
Severe aplastic anemia
Solid tumors such as neuroblastoma, breast, ovarian
Renal cell carcinoma
Autoimmune disorders, such as systemic sclerosis
Osteopetrosis
Inherited metabolic disorders
Congenital Juvenile chronic arthritis
Adrenoleukodystrophy
Amegakaryocytic thrombocytopenia
Sickle cell disease
Severe congenital immunodeficiency
Griscelli syndrome type II
Hurler syndrome
Kostmann syndrome
Krabbe disease
Metachromatic leukodystrophy
Thalassemia
Hemophagocytic lymphohistiocytosis (HLH)
Wiskott-Aldrich syndrome

EXAMPLES

The following examples are illustrative of the inventive subject matter and are not intended to be limitations thereon. These examples illustrate several aspects of the invention, as well the preferred embodiments and best mode.

Example 1

Adoptively Transferred Allogeneic T-cell Precursors Enhance T and NK Cell Reconstitution and do not Induce Graft-versus-host Disease in Syngeneic Hematopoietic Stem Cell Transplantation Recipients Applicants used OP9 bone marrow (BM) stromal cells expressing the Notch ligand DL1, the growth factor Flt3-ligand and the cytokine Interleukin-7 for the in vitro generation of large numbers of T-cell precursors, predominantly having a phenotype comparable to double negative DN-2 and DN-3 thymocytes, from lineage lin$^-$Sca-1$^+$c-kit$^{hi}$ BM-derived hematopoietic progenitor cells (see Schmitt, T. M. & Zúñiga-Pflücker, J. C. Induction of T cell development from hematopoietic progenitor cells by delta-like-1 in vitro. Immunity 17, 749-756 (2002) and Zakrzewski, J. L. et al. Adoptive transfer of T-cell precursors enhances T-cell reconstitution after allogeneic hematopoietic stem cell transplantation. Nat Med 12, 1039-1047 (2006) for a procedure for producing T-cell precursors).

In order to assess the immunotherapeutic activity of adoptively transferred in vitro-generated allogeneic T-cell precursors, Applicants infused BALB/c BM-derived lin$^-$Sca-1$^+$c-kit$^{hi}$ hematopoietic stem cells with or without C57BL/6-derived in vitro-generated T-cell precursors into lethally irradiated BALB/c hosts, and analyzed their effects on immune reconstitution and graft-versus-host disease, as well as their anti-tumor activity.

Lethally irradiated BALB/c recipients were transplanted with syngeneic purified hematopoietic stem cells (or lin$^-$ bone marrow cells); control mice received hematopoietic stem cells only, the treatment group received additional T-cell precursors generated in OP9-DL1 cocultures. In some cases, transplantation recipients were intravenously challenged with tumor cells in order to study anti-tumor activity. As shown in FIG. 1a, at days 14 and 28, Applicants found significant increases in early T and NR-cell reconstitution due to allogeneic T-cell precursors.

Figure 1B:
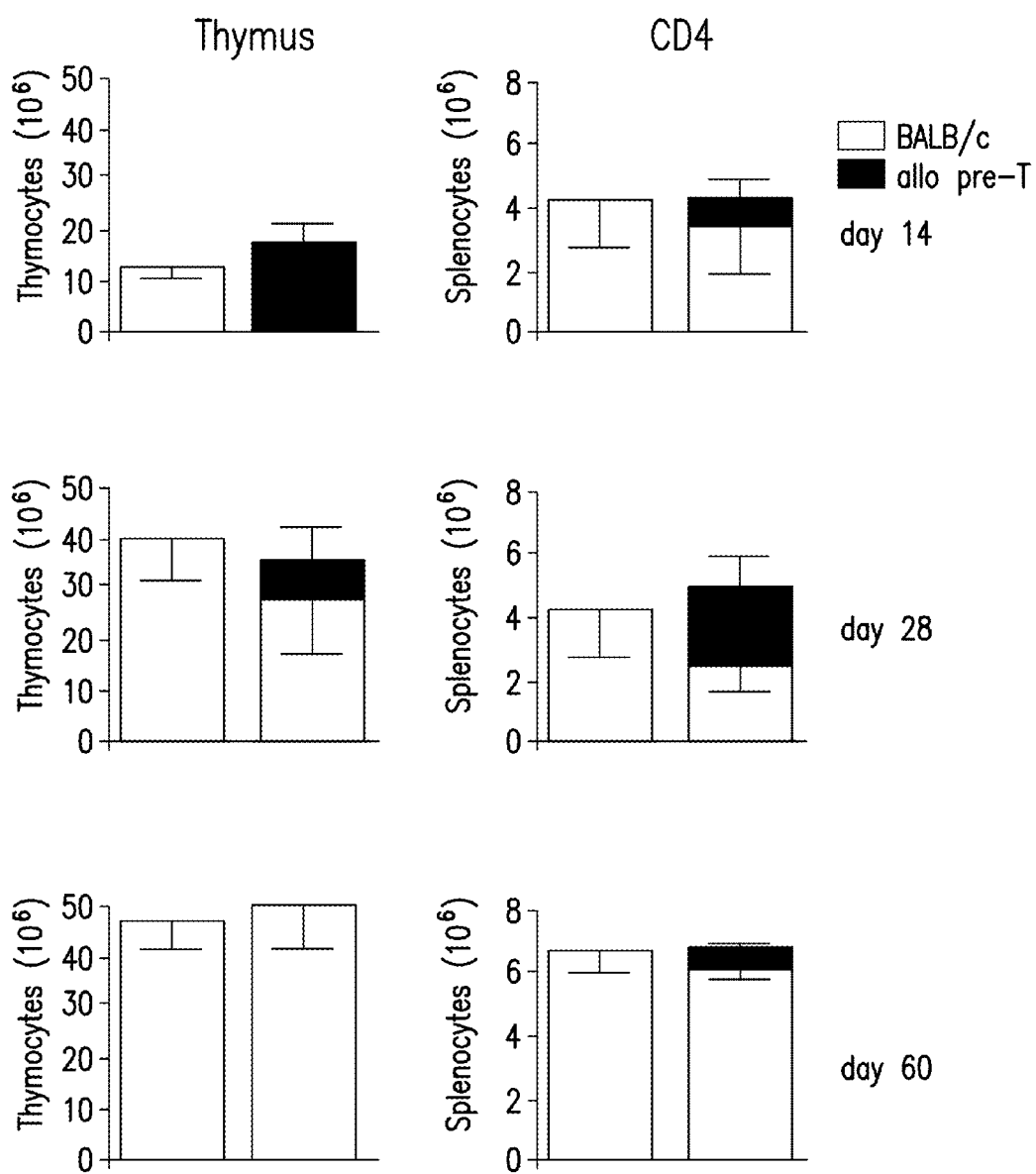
FIG. 1B is a series of bar graphs which depict BALB/c or C57BL/6 origin of cells at days 14, 28, and 60.
Figure 1B:
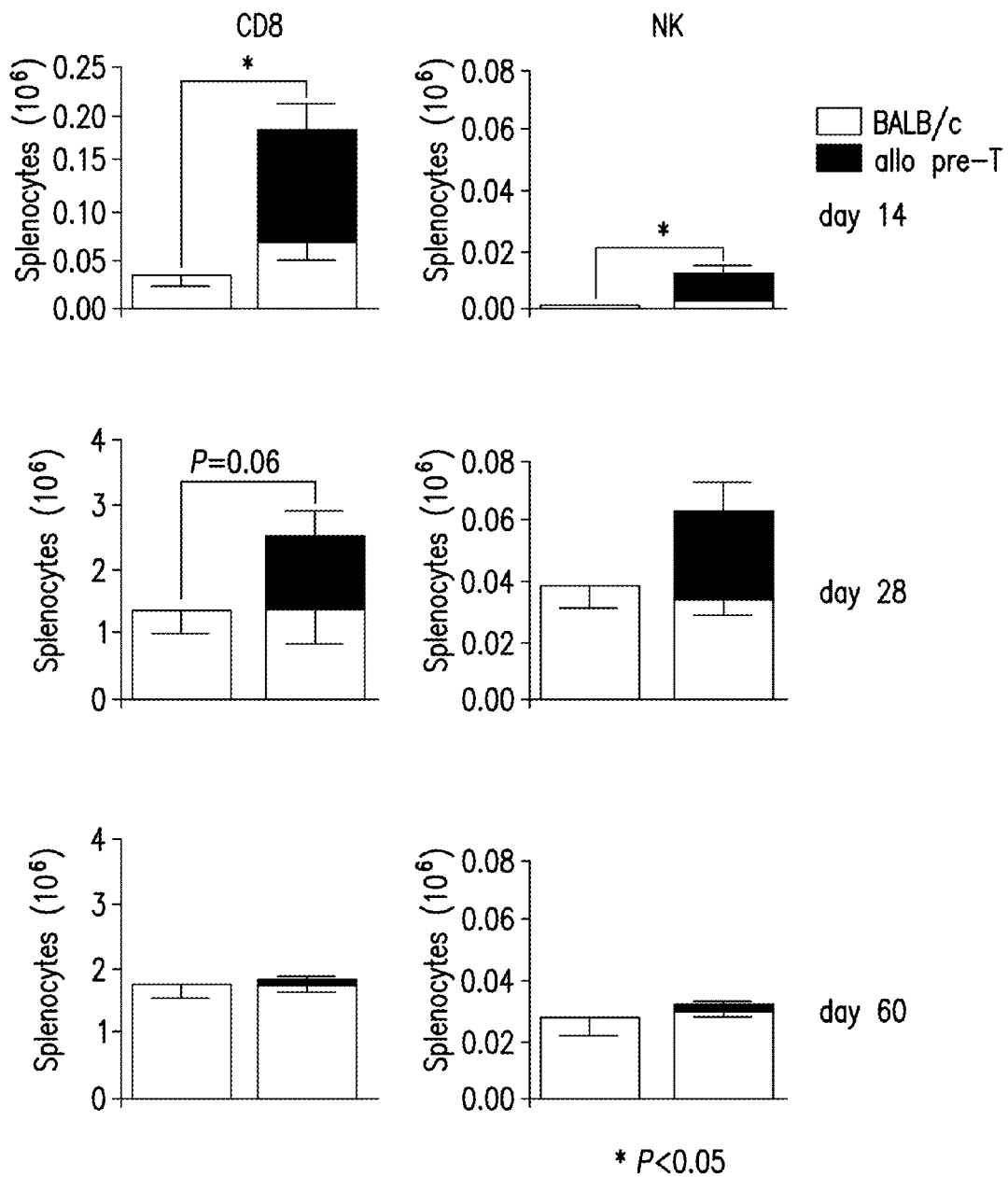

Lethally irradiated BALB/c recipients were transplanted with BALB/c hematopoietic stem cells; control mice received hematopoietic stem cells only, the treatment group received additional C57BL/6-derived in vitro-generated T-cell precursors (CD45.1$^+$). At days 14, 28, and 60 after hematopoietic stem cell transplantation, animals were sacrificed and thymi and spleens were harvested. BALB/c or C57BL/6 origin of cells was determined by total cellularity and multicolor flow cytometric analysis using Ly9.1 and CD45.1-specific antibodies. T and NK cells were analyzed using antibodies to CD3, CD4, CD8 and DX5. Combined data of more than three independent experiments are presented. Values represent mean cell numbers SEM (n=5-10). As shown in FIG. 1b, no differences between control and treatment groups at day 60 after hematopoietic stem cell transplantation were observed.

Figure 7:
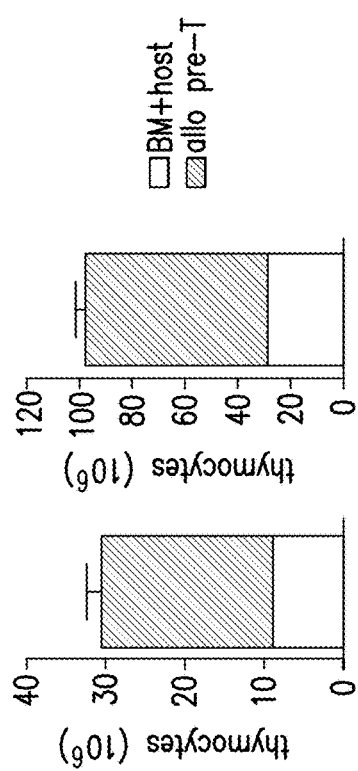
FIG. 7 is a series of graphs which depict post-transplant percentage donor and host progenies.

Importantly, as shown in FIG. 7, using syngeneic lin$^-$ BM instead of purified HSCs did hardly impair thymic engraftment of adoptively transferred allogeneic T cell precursors, illustrating the robustness of this system, demonstrating that adoptively transferred allogeneic T-cell precursors enhance thymic reconstitution in syngeneic lin– BMT recipients. Lethally irradiated BALB/c recipients were transplanted with 105 BALB/c-derived lin– BM cells and received 6×106 C57BL/6-derived T-cell precursors. Thymi were harvested on day 14 after transplantation and donor and host progenies were determined by total cellularity and multicolor flow cytometric analysis using CD45.1 and CD45-specific antibodies. Absolute numbers as well as percentages SEM are presented (n=5). The experiment was performed more than five times.

This demonstrates that adoptive transfer of allogeneic T-cell precursors results in an early wave of allogeneic T and NK cells, but does not impair long-lasting lymphoid reconstitution from autologous hematopoietic stem cells. It is noteworthy that small numbers of myeloid and dendritic cells, up to 10% of splenic CD11b+ and CD11c+ cells, originated from adoptively transferred precursor cells (data not shown).

Figure 8:
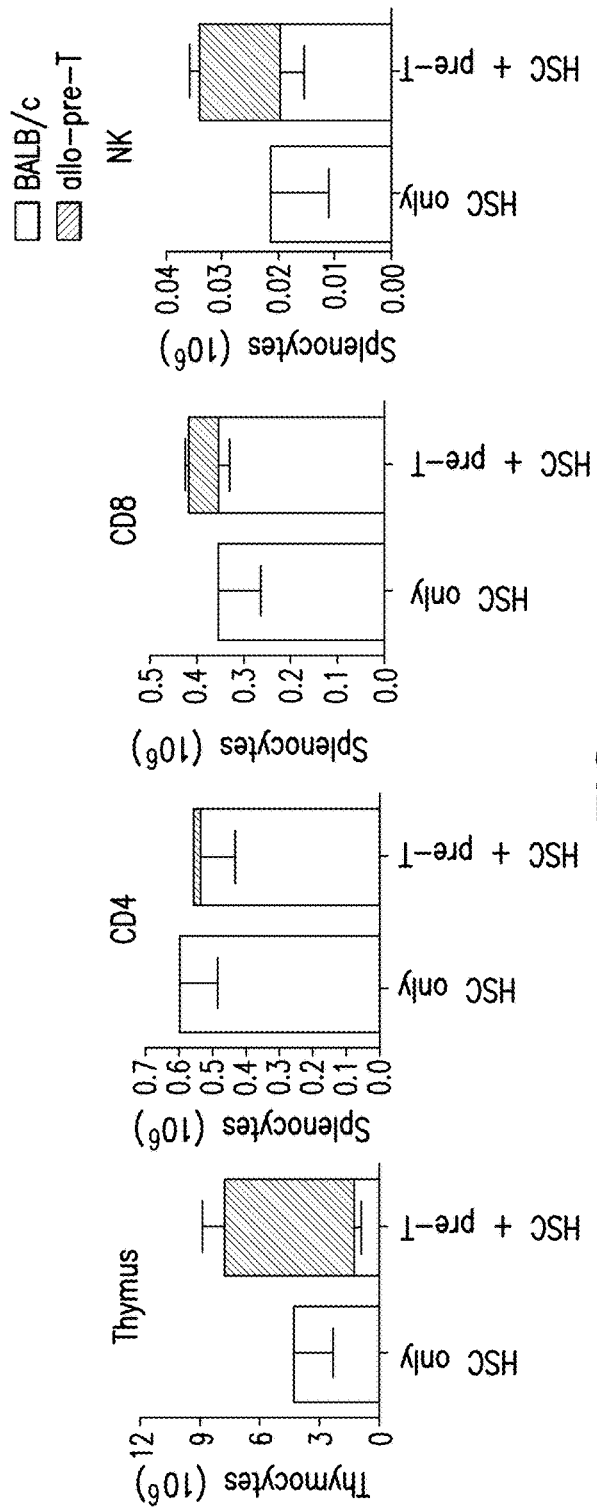
FIG. 8 is a series of graphs which depict post-transplant analysis of T and NK cells in old recipients.

In order to assess whether Applicants' approach to enhancing thymic regeneration can also be used in aging mice, Applicants transplanted one year-old mice and compared recipients of syngeneic hematopoietic stem cells alone with recipients of adoptively transferred allogeneic T-cell precursors. As shown in FIG. 8, Applicants found that transferred T-cell precursors can engraft in irradiated thymi of old mice and support reconstitution of mostly CD8+ T-cells, as well as NK cells, demonstrating that adoptively transferred allogeneic T-cell: precursors enhance thymic reconstitution in aging HSCT recipients. Lethally irradiated 12 months old BALB/c recipients were transplanted with BALB/c-derived HSCs; control mice received HSCs only, the pre-T group received additional C57BL/6-derived T-cell precursors. Thymi and spleens were harvested on day 14 after transplantation. Donor and host progenies were determined by total cellularity and multicolor flow cytometric analysis using Ly9.1 and CD45-specific antibodies, T and NK cells were analyzed using CD4, COB, CD3, and =5-specific antibodies. Mean cell numbers SEM are presented (n=4-5).

The feasibility of Applicants' approach is further illustrated by the fact that even cryopreserved allogeneic T-cell precursors display stable thymic engraftment capacity, as shown in FIG. 17, Moreover, Applicants wanted to assess if allogeneic T-cell precursors can be used for adoptive transfer in recipients that are not exposed to total body irradiation (TBI). Applicants hypothesized that targeted thymic irradiation in combination with agents that deplete recipient thymocytes and promote survival and thymic engraftment of transferred T cell precursors may be an alternative to TBI as preparative conditioning regimen.

Figure 18:
FIG. 18 is a graph depicting the cell counts and relative proportions of host cells and allogeneic T-cell precursors engrafted in the thymus of recipients of targeted thymic irradiation.

As shown in FIG. 18, Applicants were indeed able to demonstrate that allogeneic T-cell precursors can engraft in the thymus of recipients of a protocol consisting of targeted thymic irradiation, ATG and IL-7. BALB/c recipients were subjected to targeted thymic irradiation (950 cGy) 4 days prior to adoptive transfer of 8×106 C57BL/6-derived T-cell precursors. 25 mg/kg ATG was administered intraperitoneally 4 days and 1 day prior to T-cell precursor transfer. In addition, animals were treated with IL-7 (10 mg/mouse) from day 0 to day 4 after T-cell precursor transfer. Thymi were harvested 14 days after cell transfer and donor and host progenies were determined by total cellularity and multicolor flow cytometric analysis. Mean cell numbers SEM are presented (n=2).

Figure 1C:
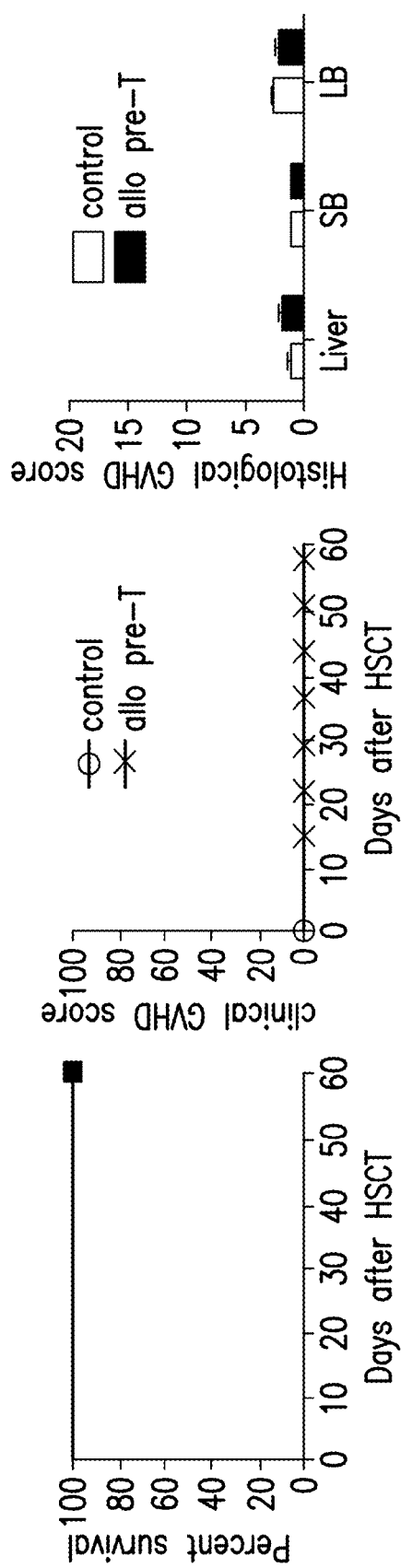
FIG. 1C is a series of bar graphs which depict post-transplantation recipient survival and GVHD scores.

Lethally irradiated BALB/c recipients were transplanted with Lin– BALB/c BM; control mice received bone marrow only, the treatment group received additional C57BL/6 T-cell precursors. Survival was monitored daily, a clinical GVHD score was monitored weekly. Histopathological analysis of signs of subclinical graft-versus-host disease in liver, small bowel and large bowel was performed eight weeks after transplantation. Data are representative of more than three independent experiments. Mean values SEM are presented (n=5). As shown in FIG. 1c, Allogeneic T-cell precursor transfer was not associated with any clinical or sub-clinical signs of graft-versus-host disease as determined by mortality, clinical GVHD score, histopathological analysis of graft-disease target organs, or weight loss (data not shown).

Example 2

Figures 2A, 2B:
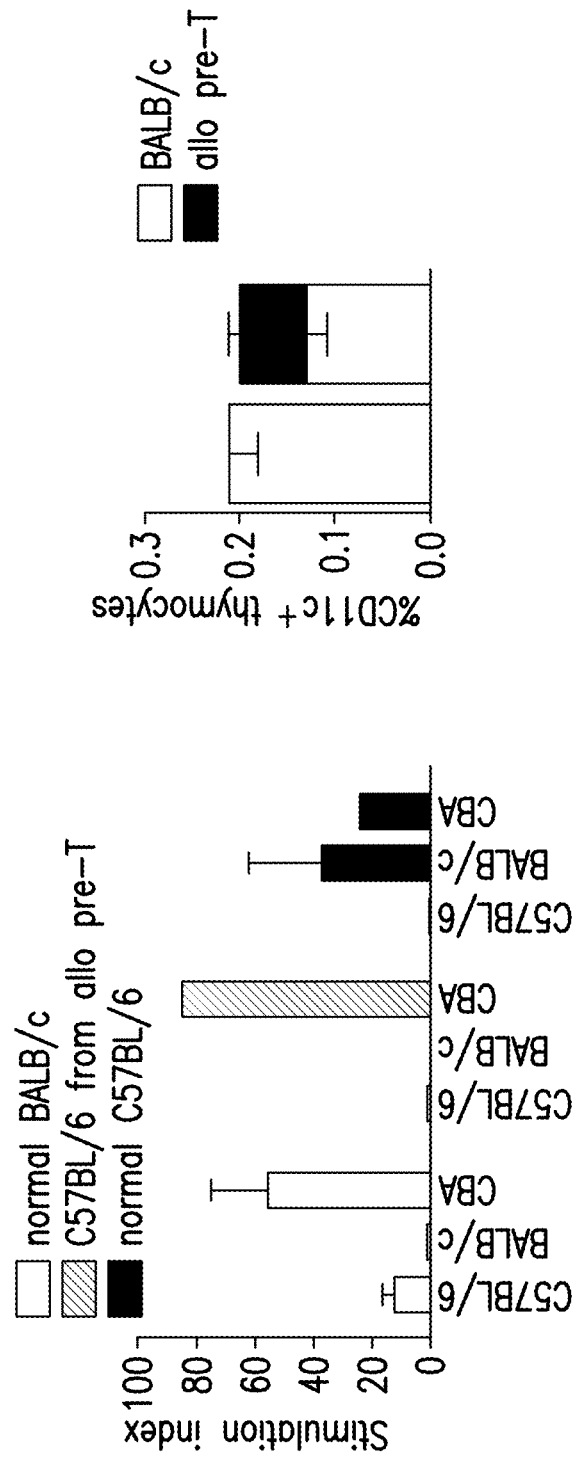
FIG. 2A is a bar graph which depicts tolerance to both host and donor, but were capable of mounting an immune response to third party antigens.
FIG. 2B is a bar graph which depicts post-transplant percent of CD11c+ cells of BALB/c and C57BL/6 origin.

TCR Selection of Adoptively Transferred Allogeneic T-cell Precursors: Adoptively Transferred Allogeneic T-cell Precursors Develop into Host MHC Restricted and Donor/Host Tolerant T-cells Lethally irradiated BALB/c recipients were transplanted with C57BL/6 hematopoietic stem cells and received additional C57BL/6-derived T-cell precursors. Animals were sacrificed at day 55-60 after hematopoietic stem cell transplantation and purified splenic T-cells of BALB/c and C57BL/6 origin were used as effector cells in Mixed Leukocyte Reaction (MLR) cultures. Normal C57BL/6 T-cells were used as additional controls. Cells were cultured for five days with irradiated C57BL/6, BALB/c, or CBA splenocytes as stimulators. Combined data of three independent experiments are presented as mean+SEM (n=8). As shown in FIG. 2a, C57BL/6 T-cells originating from adoptively transferred allogeneic T-cell precursors in syngeneic hematopoietic stem cell transplantation BALB/c recipients displayed tolerance to both host and donor, but were capable of mounting an immune response to third party antigens as determined by MLR assays, indicating that these T-cells were subject to negative and positive selection on MHC molecules of both C57BL/6 and BALB/c origin.

Lethally irradiated BALB/c recipients were transplanted with BALB/c hematopoietic stem cells and ±additional C57CL/6-derived in vitro-generated T-cell precursors. Animals were sacrificed on day 14 after HSCT and thymi were harvested for multicolor flow cytometric analysis of CD11c+ cells of BALB/c and C57BL/6 origin. Mean SEM are presented (n=5). The experiment was repeated at least three times. As shown in FIG. 2b, analysis of thymic dendritic cells (DCs) indeed revealed a mixed chimerism of 35% allogeneic DCs in recipients of allogeneic T-cell precursors, illustrating that small numbers of allogeneic antigen presenting cells (APCs) derived from the T-cell precursors make a relevant contribution to thymic negative selection.

Figure 2C:
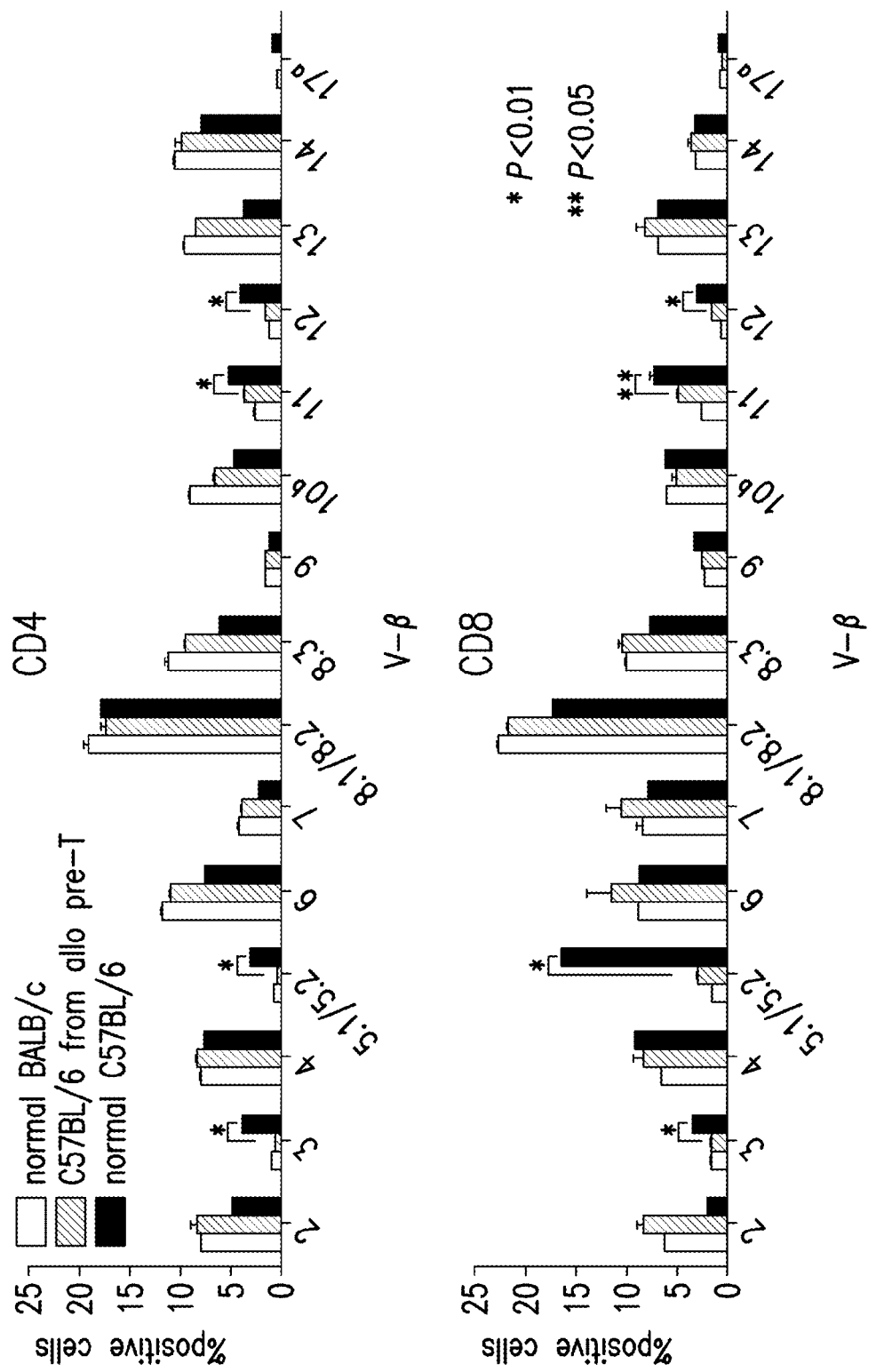
FIG. 2C is a bar graph which depicts post-transplant percent of various T-cell V-β regions.
Figure 9:
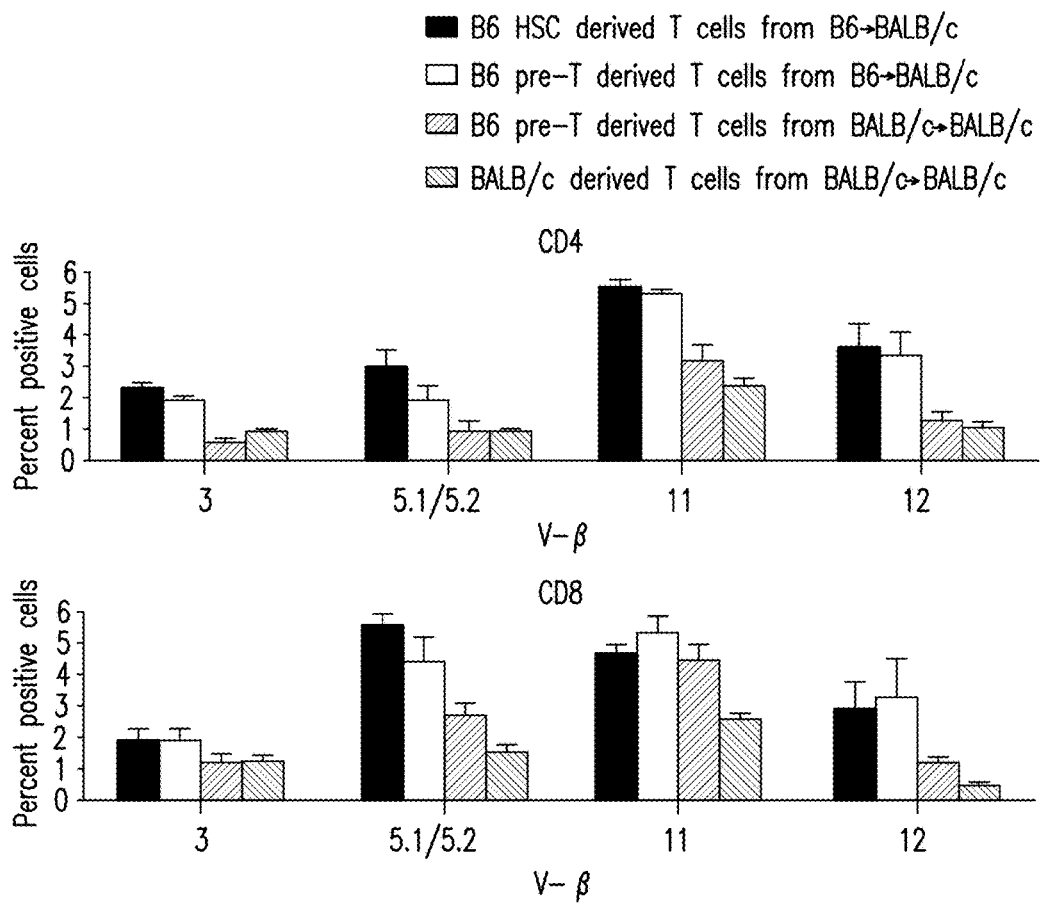
FIG. 9 is a series of graphs which depict post-transplant TCR-Vβ expression on CD4+ and CD8+ cells.

To better assess negative selection of the progeny of the adoptively transferred allogeneic T-cell precursors, Applicants determined their TCR repertoire by V-β family analysis. Lethally irradiated BALB/c recipients were transplanted with BALB/c hematopoietic stem cells and received additional C57CL/6-derived in vitro-generated T-cell precursors. Animals were sacrificed on day 60 after HSCT and splenocytes were obtained for multicolor flow cytometric analysis of the TCR-Vβ families on 004+ and CD8+ cells of C57BL/6 origin. Normal BALB/c and C57BL/6 splenocytes were used as controls. Mean+SEM are presented (n=5-8). Combined data from two independent experiments are presented. Mouse mammary tumor virus (MMTV) genes encode for superantigens that induce apoptosis of developing T-cells with a V-β region, which binds the MMTV superantigen. Due to this mechanism, V-β 3, 5.1/5.2, 11, and 12 TCR-bearing T-cells are clonally eliminated either completely or partially in BALB/c mice, but not in C57BL/6 mice. Applicants determined that the level of expression of the V-β 3, 5.1/5.2, 11, and 12 chains in recipients of C57BL/6-derived T-cell precursors in the setting of syngeneic BALB/c HSCT. FIG. 9 shows a comparison with the setting of allogeneic HSCT, while FIG. 2c shows a comparison with normal C57BL/6 and BALB/c-derived T-cells, demonstrating that negative selection of adoptively transferred allogeneic T-cell precursors in HSCT recipients is determined by donor-derived hematopoietic cells. Lethally irradiated BALB/c recipients were transplanted with BALB/c HSCs or C57BL/6 HSCs and received additional C57CL/6(CD45.1+)-derived in vitro-generated T-cell precursors. Animals were sacrificed on day 60 after HSCT and splenocytes were obtained for multicolor flow cytometric analysis of the presented TCR-V□ families on CD4+ and CD8+ cells of C57BL/6 origin. Mean±SEM are presented (n=7-8). Combined data from four independent experiments are presented.

After syngeneic hematopoietic stem cell transplantation the TCR repertoire of T-cells derived from allogeneic T-cell precursors resembles that of T-cells of syngeneic hematopoietic stem cell background and differed significantly from that of normal T-cells of allogeneic background. Using Abb/B2m double targeted mutation mice (characterized by no detectable MHC class II expression and only low levels of MHC class I expression) as hosts or stem cell donors, Applicants analyzed whether hematopoietic or non-hematopoietic cells, of donor or host origin, are responsible for positive and negative selection of adoptively transferred MHC positive allogeneic T-cell precursors.

Figure 2D:
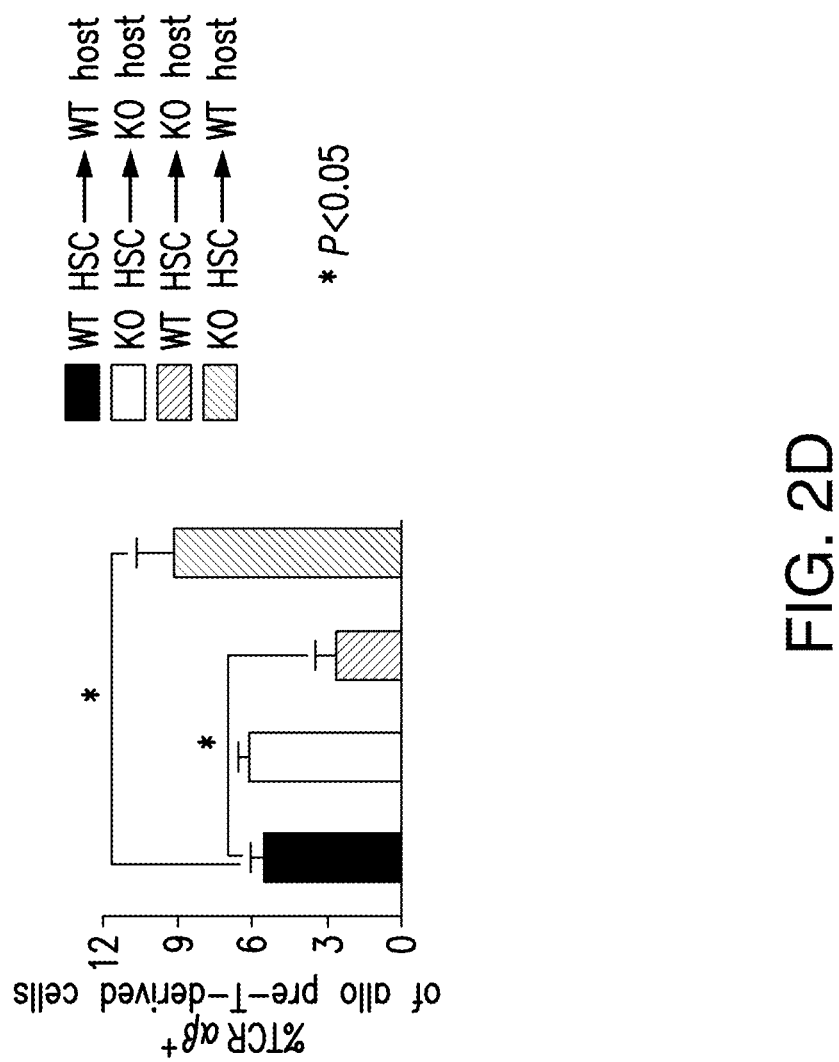
FIG. 2D is a bar graph which depicts post-transplant percent of TCR selection.

Lethally irradiated C57BL/6 wild-type recipients or C57BL/6 MHC class I and II deficient mice were transplanted with syngeneic MHC positive or MHC deficient hematopoietic stem cells. All animals received BALB/c-derived MHC positive T-cell precursors on day 0. Animals were sacrificed on day 14 after HSCT and thymocytes were obtained for multicolor flow cytometric analysis of BALB/c-derived TCRαβ$^+$ cells. Mean+SEM of combined data from two independent experiments are presented (n=4-6). As shown in FIG. 2d, significantly less TCR selection was found in MHC deficient hosts, and this failure could not be overcome by adding MHC positive syngeneic hematopoietic stem cells, indicating that positive selection of adoptively transferred allogeneic T-cell precursors depends on interaction with MHC molecules on non-hematopoietic host cells. Furthermore, when Applicants administered allogeneic T-cell precursors to (MHC$^{-/-}$→WT) chimeras, the percentage of TCRαβ$^+$ thymocytes increased significantly compared with (WT→WT) controls. This increase suggests a defect in negative selection resulting from the absence of MHC molecules on hematopoietic donor cells.

Figure 10:
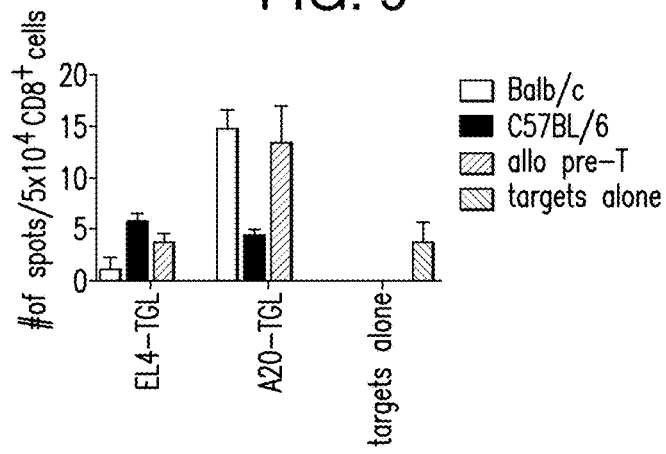
FIG. 10 is a graph which depicts INF-γ secretion by CD8+ T-cells.

Finally, as shown in FIG. 10, Applicants found in T-cell stimulation assays that CD8+ C57BL/6 T-cells originating from allogeneic T-cell precursors that had been transferred to syngeneic hematopoietic stem cell transplantation recipients (BALB/c) could recognize antigens only in the context of BALB/c MHC, but not in the context of C57BL/6 MHC. This demonstrates that CD8+ T-cells derived from adoptively transferred allogeneic T-cell precursors respond to host-MHC expressing stimulators. Lethally irradiated BALB/c (H-2d) recipients were transplanted with BALB/c Lin– BM and lethally irradiated C57BL/6 (H-2b) recipients were transplanted with C57BL/6 Lin– BM. All mice received in vitro generated C57BL/6(CD45.1+) T-cell precursors (8×106) at day 0 and were immunized with irradiated GFP-expressing OP9-DL1 cells (H-2k) at days 43 and 49 after HSCT. At day 55 after HSCT we isolated splenic CD8+ T-cells of BALB/c, C57BL/6 and allo pre-T (CD45.1+) origin and stimulated them with irradiated GFP-expressing cells of either H-2d background (A20-TGL) or H-2b background (EL4-TGL), followed by quantification of INF-□ secretion by ELISPOT. Mean+SEM are presented (n=4-7). Combined data from two independent experiments are presented.

Example 3

Adoptively Transferred Allogeneic T-cell Precursors Enhance T and NK Cell Reconstitution and Improve Survival in Irradiated Hosts In addition to syngeneic hematopoietic stem cell transplantation recipients, Applicants also infused allogeneic (C57BL/6-derived) T-cell precursors into BALB/c mice receiving sublethal or lethal irradiation doses without stem cell rescue.

Figure 3A:
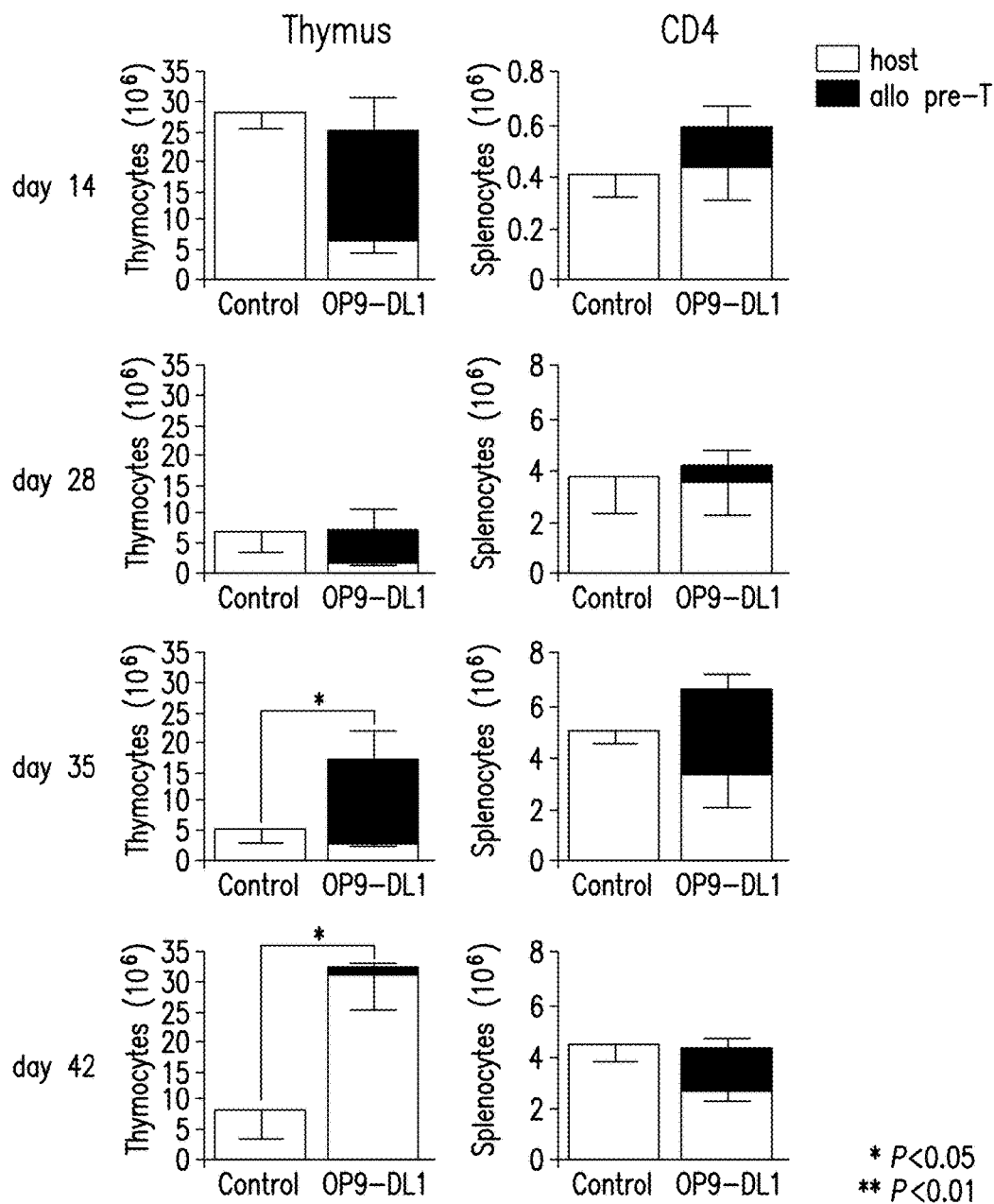
FIG. 3A is a series of bar graphs which depict BALB/c or C57BL/6 origin of cells, and early T and NK-cell reconstitution.
Figure 3A:
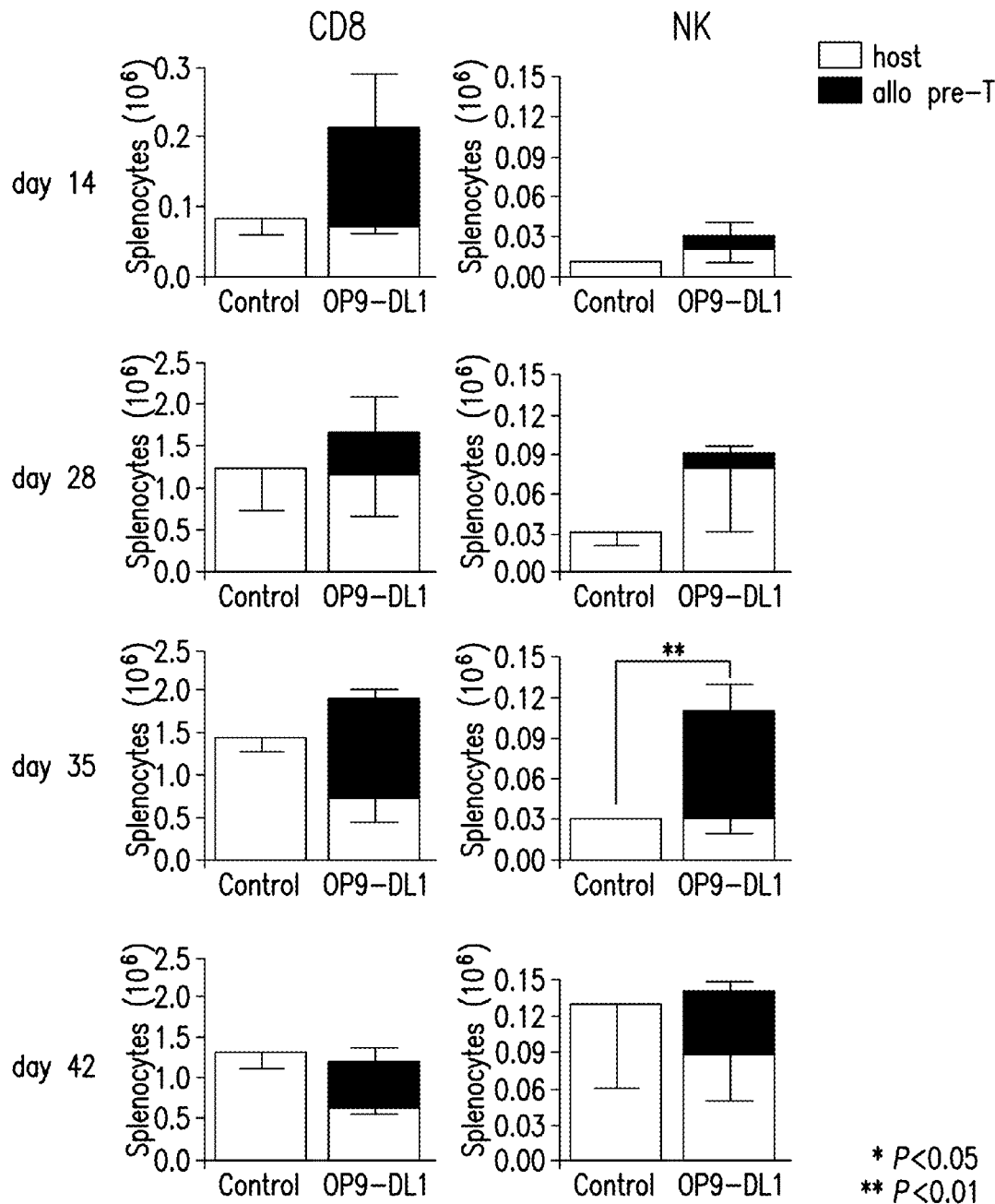
Figure 3B:
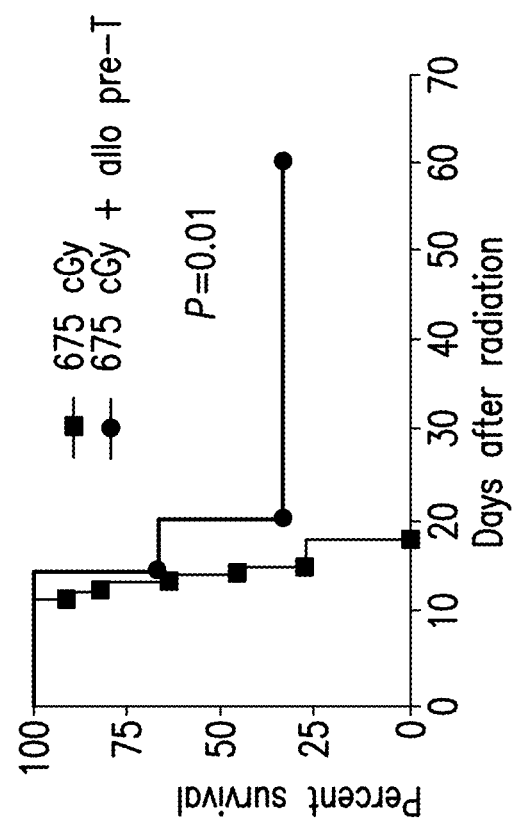
FIG. 3B is a graph which depicts post-transplant percent survival of irradiated transplant recipients.

BALB/c recipients were irradiated with a single dose of 650-687 cGy. Control mice received irradiation only; the treatment group received additional C57BL/6-derived in vitro-generated T-cell precursors. At days 14, 28, 35, and 42 after irradiation animals were sacrificed and thymi and spleens were harvested. BALB/c or C57BL/6 origin of cells was determined by total cellularity and multicolor flow cytometric analysis using Ly9.1 and CD45.1-specific antibodies. T and NK cells were analyzed using antibodies to CD3, CD4, CD8 and DX5. Values represent mean cell numbers SEM (n=5-12). Similarly, BALB/c recipients were irradiated with a single dose of 675 cGy. Control mice received irradiation only; the treatment group received additional 057BL/6-derived in vitro-generated T-cell precursors. Survival was monitored daily. One of three independent experiments is presented (n=6-11). Combined data of two independent experiments are presented. As shown in FIG. 3a and FIG. 3b, respectively, this resulted in enhanced early T and NK-cell reconstitution and significantly improved survival. Consistent with Applicants' findings in the allogeneic setting (see Zakrzewski, J. L. et al. Adoptive transfer of T-cell precursors enhances T-cell reconstitution after allogeneic hematopoietic stem cell transplantation. Nat Med 12, 1039-1047 (2006)), thymopoiesis was significantly increased in the treatment group compared with the control group, even after the wave of allogeneic cells had left the thymus, demonstrating an additional benefit of T-cell precursor administration on thymic reconstitution because of lymphostromal interaction. Applicants expect that this shows positive feedback and cross talk between developing thymocytes and thymic stroma.

Example 4

Graft-versus-tumor Activity of Adoptively Transferred Allogeneic T-cell Precursors: Adoptively Transferred Allogeneic T-cell Precursors Enhance Graft-versus-tumor Activity in Syngeneic Hematopoietic Stem Cell Transplantation Recipients To assess the efficacy of allogeneic T-cell precursors for tumor immunotherapy, Applicants adoptively transferred C57BL/6-derived T-cell precursors, along with BALB/c HSCs, into lethally irradiated BALB/c hosts that were challenged with bioluminescent tumor cells.

Figure 4A:
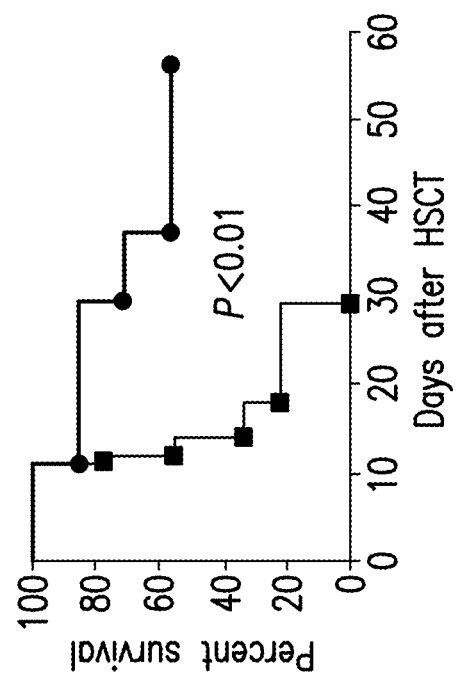
FIG. 4A is a graph which depicts post-transplant percent survival for A20-TGL lymphoma cell recipients.
Figure 4B:
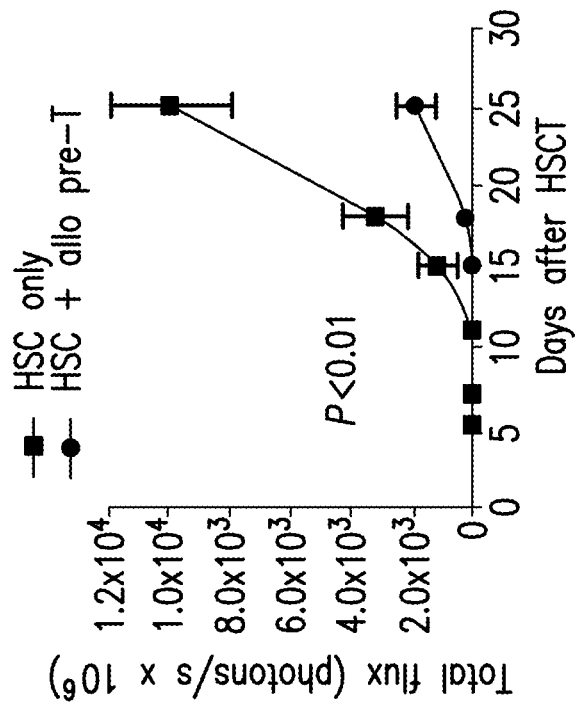
FIG. 4B is a graph which depicts post-transplant BLI for A20-TGL lymphoma cell recipients.
Figure 4C:
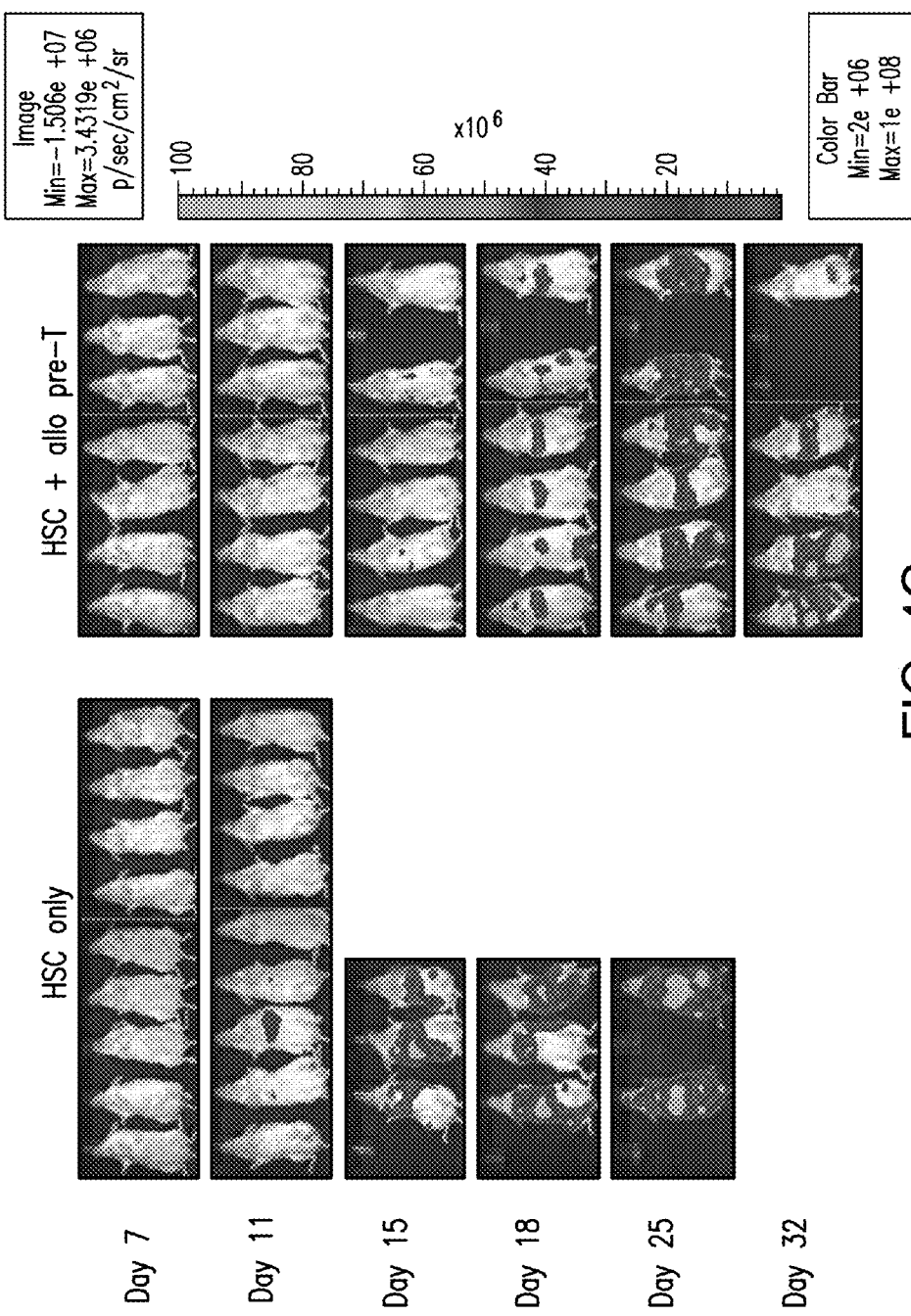
FIG. 4C is a series of photographs which depicts post-transplant BLI for A20-TGL lymphoma cell recipients.

Lethally irradiated BALB/c recipients were transplanted with BALB/c hematopoietic stem cells; control mice received hematopoietic stem cells only, the treatment group received additional C57BL/6-derived in vitro-generated T-cell precursors. All mice received 2.5×10$^5$ luciferase-expressing A20-TGL tumor cells on day 0. Over the course of 32 days after injection the whole body distribution of transduced tumor cells was monitored using in vivo bioluminescence imaging. Survival is shown in (A), the bioluminescent signal intensity for every group at six time points presented as mean SEM is shown in (B) and pseudo-color images superimposed on conventional photographs are shown in (C) (n=7-9). As shown in FIGS. 4a-4c for A20-TGL lymphoma cells, significant anti-tumor activity was found compared with recipients of hematopoietic stem cells only, as determined by survival and in vivo bioluminescent imaging.

Figure 4E:
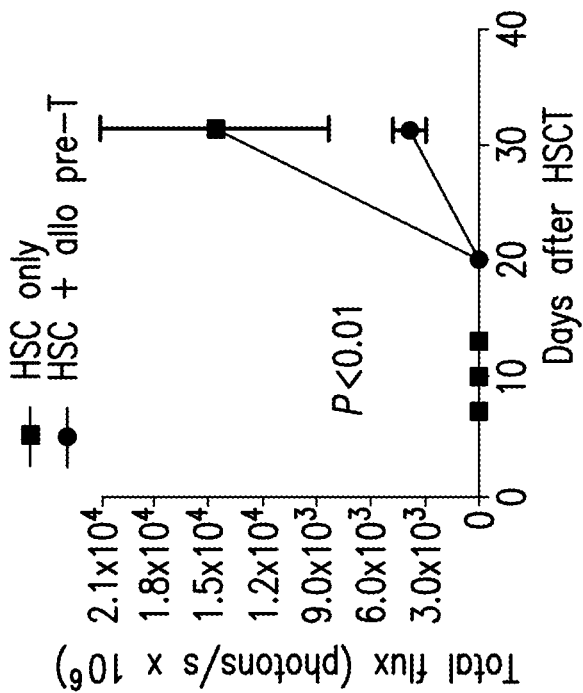
FIG. 4E is a graph which depicts post-transplant BLI for Renca-TGL renal cell carcinoma recipients.
Figure 4D:
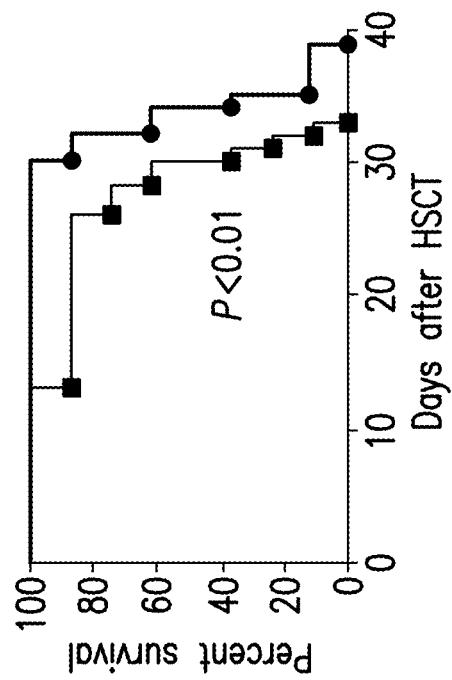
FIG. 4D is a graph which depicts post-transplant percent survival for Renca-TGL renal cell carcinoma recipients.

Similarly, lethally irradiated BALB/c recipients were transplanted with BALB/c hematopoietic stem cells; control mice received hematopoietic stem cells only, the treatment group received additional C57BL/6-derived in vitro-generated T-cell precursors. All mice received $5 \times 10^4$ luciferase-expressing Renca-TGL tumor cells on day 0. Over the course of days after injection the whole body distribution of transduced tumor cells was monitored using in vivo bioluminescence imaging. Survival is shown in (D) and the bioluminescent signal intensity for every group at five time points presented as mean+SEM is shown in (E) (n=7-9). Experiments were performed at least twice. As shown in FIGS. 4d and 4e for Renca-TGL renal cell carcinoma cells, significant anti-tumor activity was found compared with recipients of hematopoietic stem cells only, as determined by survival and in vivo bioluminescent imaging.

Further, as shown in FIG. 11 in the context of sublethal irradiation in the absence of syngeneic HSCT, Applicants found the same benefit: significant anti-tumor activity was found. This demonstrates that anti-tumor responses of adoptively transferred allogeneic T-cell precursors in sublethally irradiated recipients depend on the immunogenicity of the tumor. Sublethally irradiated (625 cGy) BALB/c recipients were challenged with 2.5×105 A20, A20-hCD19 or A20-TGL tumor cells i.v. on day. 0 □ administration of 6×106 allogeneic T-cell precursors (control groups versus allo pre-T groups). Survival was monitored daily (A) and in recipients of A20-TGL cells tumor growth was monitored by in vivo BLI (B) (n=5-7).

Example 5

The Efficacy of Adoptively Transferred T-cell Precursors in Syngeneic Hematopoietic Stem Cell Transplantation Recipients Depends on the Immunogenicity of the Tumor but not on MHC Disparity Lethally irradiated BALB/c recipients were transplanted with BALB/c hematopoietic stem cells; control mice received hematopoietic stem cells only, the treatment groups received additional C57BL/6-derived in vitro-generated T-cell precursors. All mice received $2.5 \times 10^5$ tumor cells on day 0, either A20-TGL or A20 cells, and survival was monitored (n=8). As shown in FIG. 5a, graft-versus-tumor activity of adoptively transferred allogeneic T-cell precursors against A20-TGL cells (immunogenic, due to expression of herpes simplex thymidine kinase, firefly luciferase, and GFP) or less immunogenic A20 cells, produced a survival benefit only in the A20-TGL group. These results demonstrate that the anti-tumor activity of T-cell precursors is related to the expression of immunogenic tumor-associated antigens or neoantigens such as TGL, and that syngeneic T-cell precursors would be able to mediate anti-tumor activity, provided the targeted tumor was strongly immunogenic.

Lethally irradiated BALB/c recipients were transplanted with BALB/c hematopoietic stem cells; control mice received hematopoietic stem cells only, the treatment groups received additional C57BL/6 or BALB/c-derived in vitro-generated T-cell precursors. All mice received $2.5 \times 10^5$ A20-TGL tumor cells on day 0. Over the course of 25 days after injection the whole body distribution of luciferase expressing tumor cells was monitored using in vivo bioluminescence imaging. The bioluminescent signal intensity for every group at seven time points presented as mean+SEM (n=6-8). As shown in FIG. 5b, using the same syngeneic hematopoietic stem cell transplantation model and A20-TGL tumor cells. Applicants have demonstrated that allogeneic and syngeneic T-cell precursor transfers resulted in the same degree of anti-tumor activity. This underscores the importance of immunogenicity for a strong T-cell response.

Lethally irradiated BALB/c recipients were transplanted with BALB/c hematopoietic stem cells, received additional C57BL/6-derived in vitro-generated T-cell precursors and were challenged with $2.5 \times 10^5$ A20-TGL tumor cells on day 0. On days 27 to 32 after HSCT, animals were sacrificed and splenic T-cells were cultured over night in the presence of soluble CD28-specific antibodies±irradiated A20 cells, A20-TGL cells or immobilized antibodies directed against CD3. Cells were stained for CD45.1, CD4, CD8, IFN-γ and rat IgGl-κ (isotype control) and analyzed for IFN-γ expression on C57BL/6-derived CD4+ and CD8+ T-cells. Combined data of three independent experiments are shown. Mean values+SEM are presented (n=10-12). As shown in FIG. 5c, T-cells derived from adoptively transferred allogeneic T-cell precursors responded with more IFN-γ secretion upon in vitro stimulation with A20-TGL cells compared with stimulation with A20 cells. In addition, the findings presented in FIG. 10, including weak response of C57BL/6 T cells to EL4-TGL compared with a strong response of BALB/c and allo pre-T-derived T cells to A20-TGL, suggest an important role of costimulatory molecules for potent anti-tumor responses, since A20 cells highly express CD86 and lack CD80 whereas EL4 cells show only weak expression of CD86 and lack CD80 (data not shown).

As was shown in FIG. 2a and discussed above, adoptive transfer of T-cell precursors also results in early reconstitution of NK cells. In order to assess the possible contribution of NK cells to anti-tumor activity against A20-TGL cells, Applicants compared syngeneic HSCT recipients receiving allogeneic precursor cells±NK cell-depleting antibody treatment. Lethally irradiated BALB/c recipients were transplanted with BALB/c hematopoietic stem cells; control mice received hematopoietic stem cell only, the treatment groups received additional C57BL/6-derived in vitro-generated T-cell precursors±NK1.1 depleting antibodies. All groups received $0.25 \times 10^6$ A20-TGL tumor cells on day 0. At the indicated time points, tumor growth was determined by in vivo bioluminescence imaging and is presented as mean+SEM (n=6-8). As shown in FIG. 5d, depletion of NK cells derived from adoptively transferred precursor cells had only a minor effect on graft-versus-tumor activity.

Figure 12:
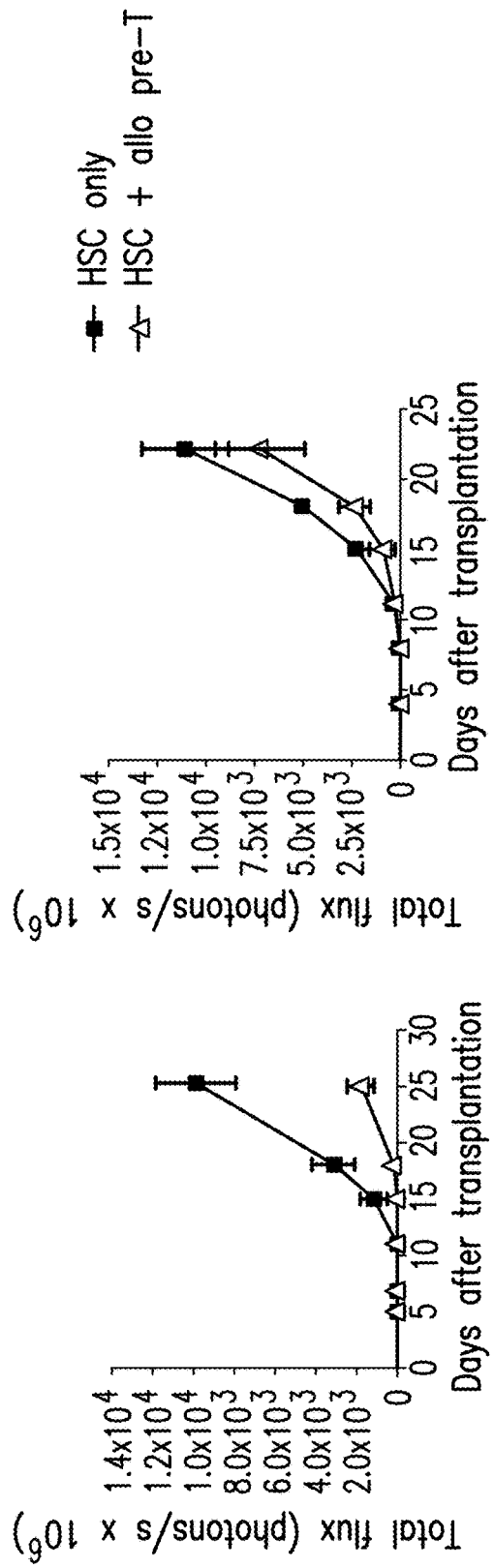
FIG. 12 is two graphs which depict BLI of A20-TGL tumor cell-challenged recipients.

Applicants also found that, as shown in FIG. 12, that with increasing tumor burdens, the anti-tumor effect becomes less effective. This demonstrates that anti-tumor responses of adoptively transferred allogeneic T-cell precursors in are less effective in advanced tumors. Lethally irradiated BALB/c mice received 103 syngeneic HSCs and were challenged with 2.5×105 A20-TGL or 5×105 A20-TGL tumor cells i.v. on day, 0 □ administration of 8×106 allogeneic T-cell precursors. Tumor growth was monitored by in vivo BLI (n=5-8).

Thus, in general, but particularly in the setting of advanced and poorly immunogenic tumors, T-cell precursors are unlikely to eradicate a tumor completely if they are not combined with additional therapeutic modalities such as radiotherapy, chemotherapy, or molecular therapy.

To emulate more clinically relevant settings, Applicants therefore challenged mice with A20-TGL cells six days before adoptive immunotherapy with allogeneic T-cell precursors combined with 650 cGy-dose radiotherapy. BALB/c recipients were irradiated with 250 cGy and received 2.5× $10^5$ A20-TGL cells i.v. on day −6. On day 0, all mice received a second radiation dose of 650 cGy and were transplanted with BALB/c HSCs. Control mice received HSCs only, the treatment group received additional C57BL/6-derived in vitro-generated T-cell precursors on day 0. At the indicated time points, tumor growth was determined by in vivo BLI and is presented as mean+SEM (n=6-7).

Figure 5E:
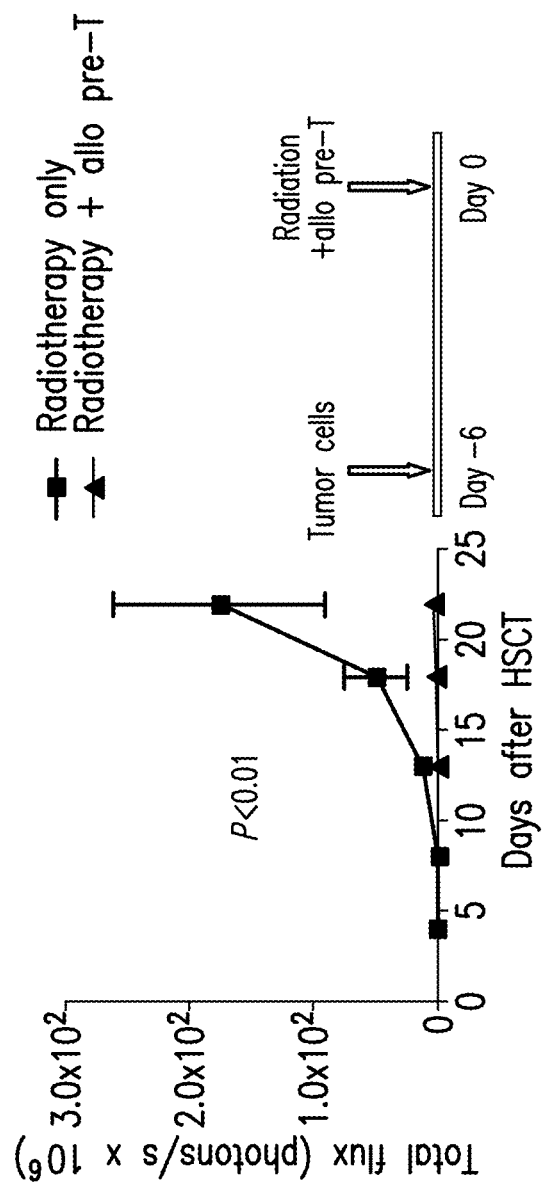
FIG. 5E is a graph of post-transplant BLI which depicts synergistic effects of combined immunotherapy.

This model allowed us not only to assess the efficacy of this combination treatment, but it also addresses an important issue of thymic negative selection, since in this setting T-cell precursors expressing TCRs specific for tumor-associated antigens would be expected to be more likely to be subjected to negative selection. However, as shown in FIG. 5e, very strong anti-tumor activity that exceeded the effect of adoptive immunotherapy in our conventional tumor experiments by approximately 20-fold less tumor growth by day 27 compared to recipients of radiation alone, indicating the selection of a functional TCR repertoire and synergistic effects of combined radio and T-cell precursor immunotherapy. In particular in the setting of advanced and poorly immunogenic tumors, T-cell precursors are unlikely to eradicate a tumor completely if not genetically engineered to be antigen-specific and combined with additional therapeutic modalities such as radiotherapy, chemotherapy or molecular therapy.

Example 6

Genetically Engineered Antigen-specific T-cell Precursors Give Rise to Functional CD8 and CD4 Positive T-cells Coexpressing Chimeric Antigen Receptor and Endogenous TCR TCR gene or antigen receptor gene transfer has been used as a strategy to induce antigen-specific T-cell immunity and has shown remarkable success in the treatment of malignancies in preclinical models. Since many malignant tumors are not very immunogenic, it would therefore be highly desirable to generate tumor antigen-specific precursor cells. In order to allow positive selection of transduced precursor cells, it is important to transfer a gene that does not interfere with endogenous TCR expression and selection. Thus, instead of TCR gene transfer, Applicants therefore retrovirally engineered T-cell precursors to stably express a chimeric antigen receptor designated 19z1, which consists of an extracellular antigen-binding domain targeting human CD19, derived from an anti-CD19 antibody, and an intracellular signal transduction domain derived from human CD3-ζ. Use of this CAR enables antigen recognition in an MHC independent manner.

The 19z1 chimeric antigen receptor has previously been used to genetically engineer peripheral blood-derived human T-cells, targeting disseminated intramedullary tumors in immunodeficient mice.

Figure 13:
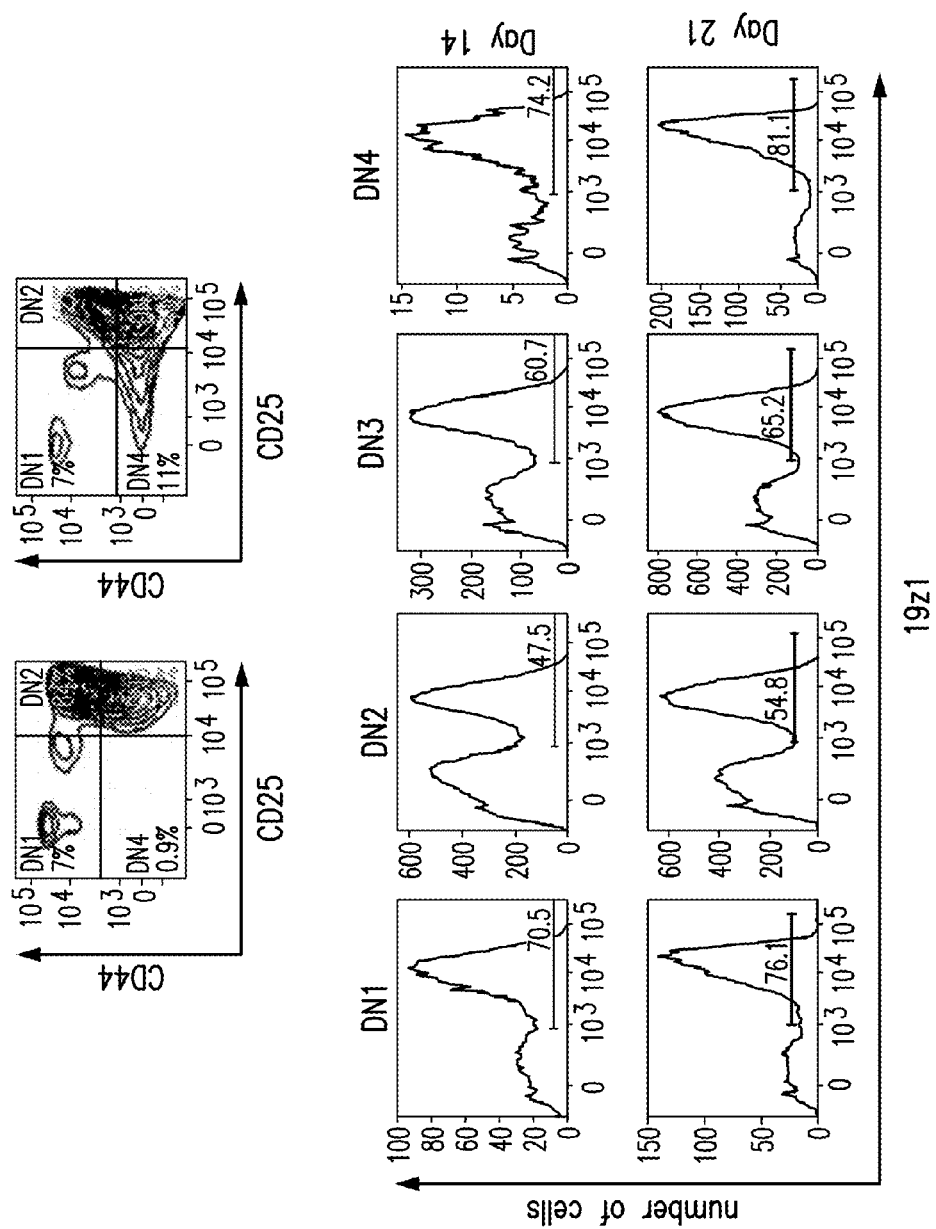
FIG. 13 is a series of graphs which depict 19z1 expression for DN1 to DN4 cell stages.

As shown in FIG. 13, transduction efficiencies of the DN2 subset, which is the relevant subset for thymic engraftment, were routinely in the range of 50% and up to 70-80% in DN1 and DN4 cells by day 21 of culture. In order to assess the feasibility of anti-tumor therapy with tumor-specific T-cell precursors, Applicants adoptively transferred 19z1-transduced allogeneic T-cell precursors to syngeneic hematopoietic stem cell transplantation recipients and analyzed their progeny at days 27 and 40 after transplantation. This demonstrates that T-cell precursors can be genetically engineered to be antigen-specific. OP9-DL1-derived C57BL/6 T-cell precursors on days 5 and 6 of coculture were retrovirally transduced with a 19z1-encoding lentiviral vector and cells from days 14 and 21 of coculture were analyzed by multicolor flow cytometry. Cells were gated on the CD4/CD8 DN population and further resolved into the DN1 to DN4 stages based on expression of CD44 and CD25. DN1-0N4 T-cell precursors were then analyzed for expression of 19z1. A representative example of six experiments is presented.

Figure 14:
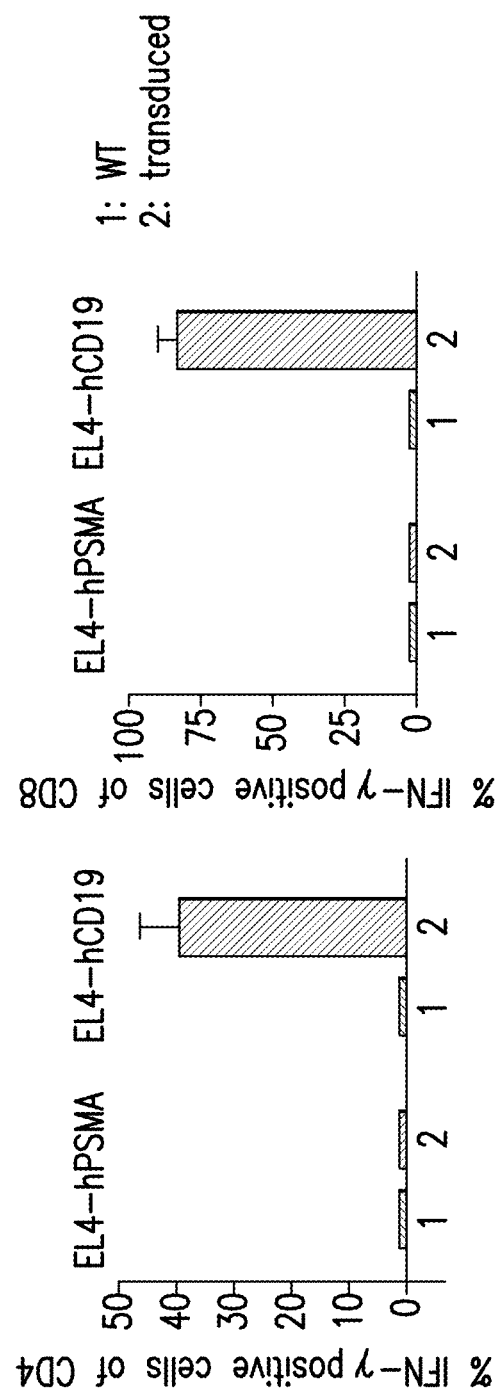
FIG. 14 is two graphs which depict IFN-γ expression on CD4+19z1−, CD4+19z1+, CD8+19z1− and CD8+19z1+ T-cells.

As shown in FIG. 14, progeny of 19z1-expressing but not progeny of 19z1-negative T-cell precursors respond to stimulation with hCD19-expressing target cells. Lethally irradiated BALB/c recipients were transplanted with BALB/c HSCs and received additional C57BL/6(CD45.1)-derived in vitro-generated T-cell precursors transduced to express 19z1. Animals were immunized with irradiated A20-hCD19 cells on day 32 after HSCT. On day 40 after HSCT, animals were sacrificed and splenic T-cells were cultured overnight in the presence of soluble CD28-specific antibodies+irradiated EL4-hPSMA cells or EL4-hCD19 cells. Cells were stained for CD45.1, CD4, CD8, 19z1 and IFN-□ and analyzed for IFN-D expression on C57BL/6-derived CD4+19z1−, CD4+19z1+, CD8+19z1− and CD8+19z1+ T-cells. Mean values+SEM are presented (n=5).

Figure 15:
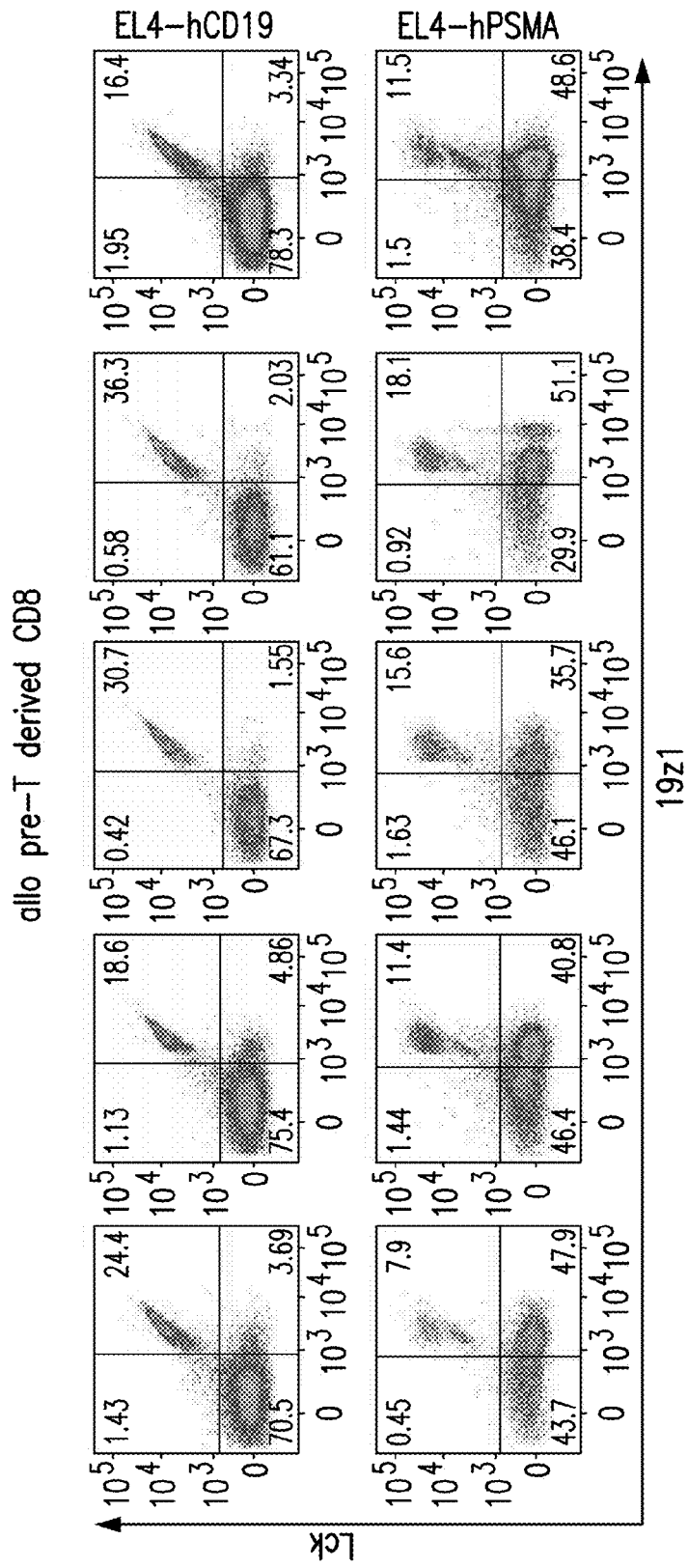
FIG. 15 is a series of graphs which depict flow cytometry analysis of CD45.1, CD8, 19z1 and Lck expression.

As shown in FIG. 15, progeny of 19z1-expressing but not progeny of 19z1-negative T-cell precursors respond with increased Lck recruitment to stimulation with hCD19-expressing target cells. Lethally irradiated BALB/c recipients were transplanted with BALB/c HSCs and received additional C57BL/6(CD45.1)-derived in vitro-generated T-cell precursors transduced to express 19z1. Animals were immunized with irradiated A20-hCD19 cells on day 46 after HSCT. On day 56 after HSCT, animals were sacrificed and splenic T-cells were stimulated by irradiated EL4-hPSMA cells or EL4-hCD19 cells. Cells were stained with antibodies specific for CD45.1, CD8, 19z1 and Lck and analyzed for intracellular Lck expression on C57BL/6-derived CD8+19z1− and CD8+19z1+ T-cells (n 5).

Figure 6A:
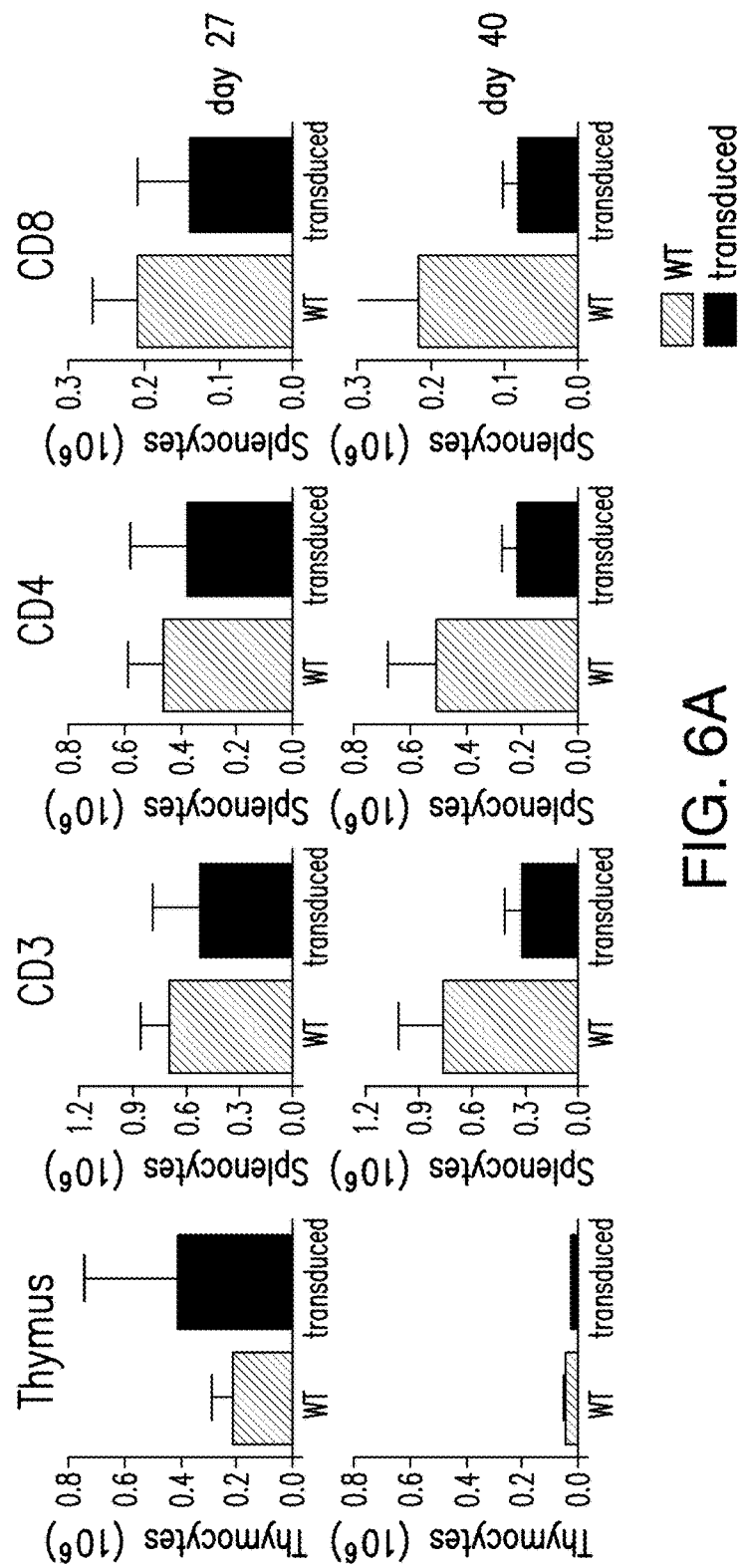
FIG. 6A is a series of bar graphs which depict post-transplant percentage of transduced DN2 cells.

Lethally irradiated BALB/c recipients were transplanted with BALB/c hematopoietic stem cells and received additional C57BL/6(CD45.1)-derived in vitro-generated T-cell precursors transduced to express 19z1. At days 27 and 40 after HSCT, animals were sacrificed and thymi and spleens were harvested. C57BL/6 origin of cells was determined by total cellularity and multicolor flow cytometric analysis using CD45.1-specific antibodies. T-cells were analyzed using antibodies to CD3, CD4, CD8 and 19z1. Values represent mean cell numbers+SEM (n=5). One of three independent experiments is presented. As shown in FIG. 6a, both CD3+CD4+ and CD3+CD8+19z1-expressing peripheral T-cells were found in these animals. The percentage of transduced T-cells of allogeneic origin corresponded with the percentage of transduced DN2 cells in the cultures that had been used for adoptive transfer, suggesting normal positive and negative selection of transduced T-cell precursors.

Lethally irradiated BALB/c recipients were transplanted with BALB/c hematopoietic stem cells and received additional C57BL/6-derived in vitro-generated T-cell precursors transduced to express 19z1. At day 27 after HSCT, animals were sacrificed and splenocytes were obtained for multicolor flow cytometric analysis of the TCR-Vβ families on CD4+ and CD8+ cells of C57BL/6 origin. Mean+SEM are presented (n=3). As shown in FIG. 6b, TCR repertoire analysis revealed no difference between transduced and untransduced cells.

Lethally irradiated BALB/c recipients were transplanted with BALB/c hematopoietic stem cells only or received additional, either unmanipulated or genetically engineered 19z1-expressing, C57BL/6-derived T-cell precursors. All mice received $2.5 \times 10^5$ A20-hCD19 cells i.v. on day 0, and survival was monitored daily. Tumor death was confirmed by necropsy and hCD19 expression of killing tumors was confirmed by flow cytometric analysis. Combined data of two independent experiments are presented (n=13). As shown in FIG. 6c, and Supplementary FIGS. 8 and 9, in vitro stimulation with target T-cells expressing hCD19 or an irrelevant antigen (hPSMA) revealed a strong interferon-γ response, as well as increased Lck recruitment, to hCD19 in 19z1-transduced T-cells compared to wild-type C67BL/6 T-cells. Importantly, expression of hCD19 by A20 did not result in a significant increase in immunogenicity, as shown in FIG. 11. Indeed, survival was significantly improved in recipients of transduced T-cell precursors compared with recipients of wild-type T-cell precursors or of hematopoietic stem cells only.

Figure 6D:
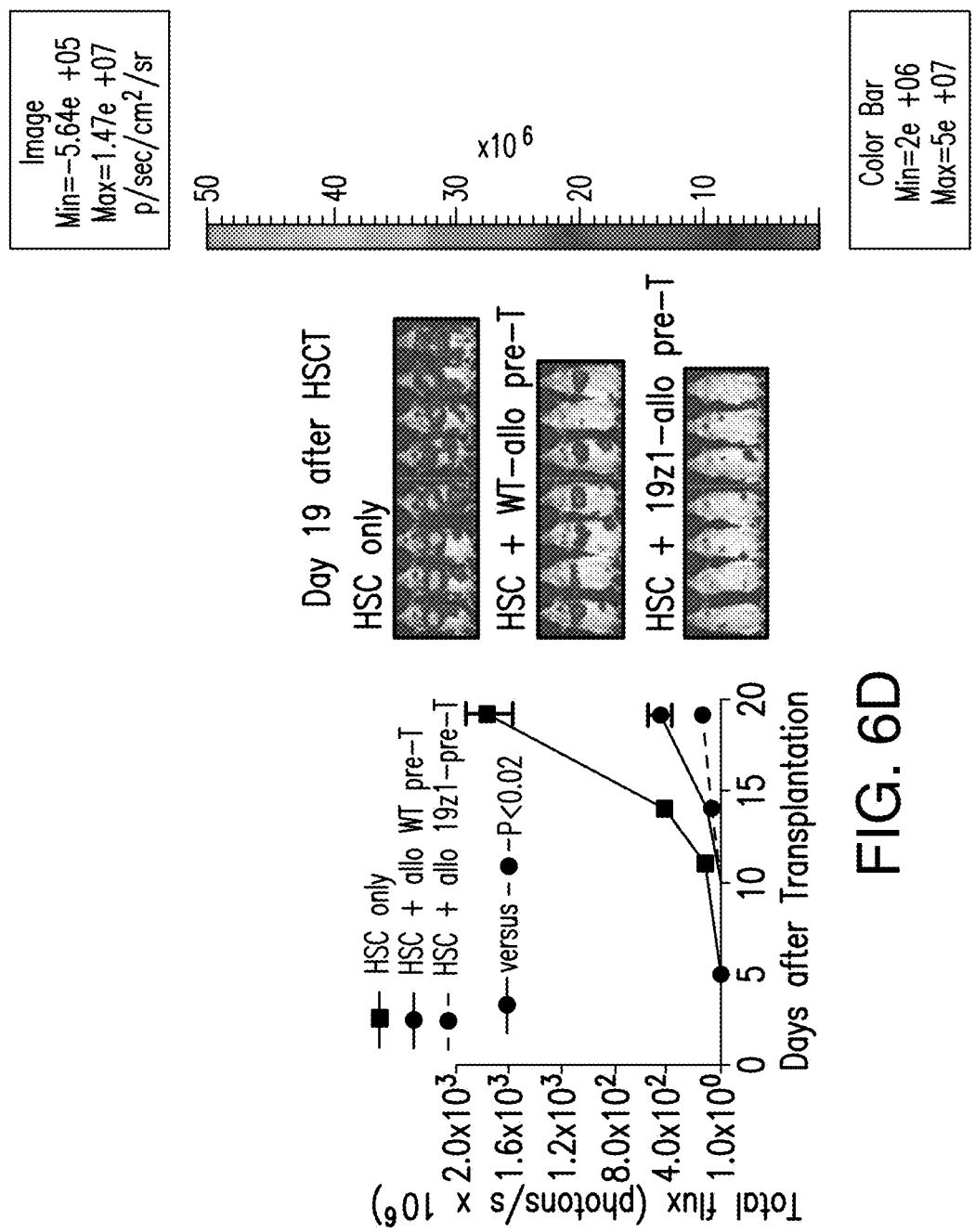
FIG. 6D depicts anti-tumor activity in recipients of 19z1-expressing T-cell precursors compared with recipients of untransduced T-cell precursors.
Figure 16:
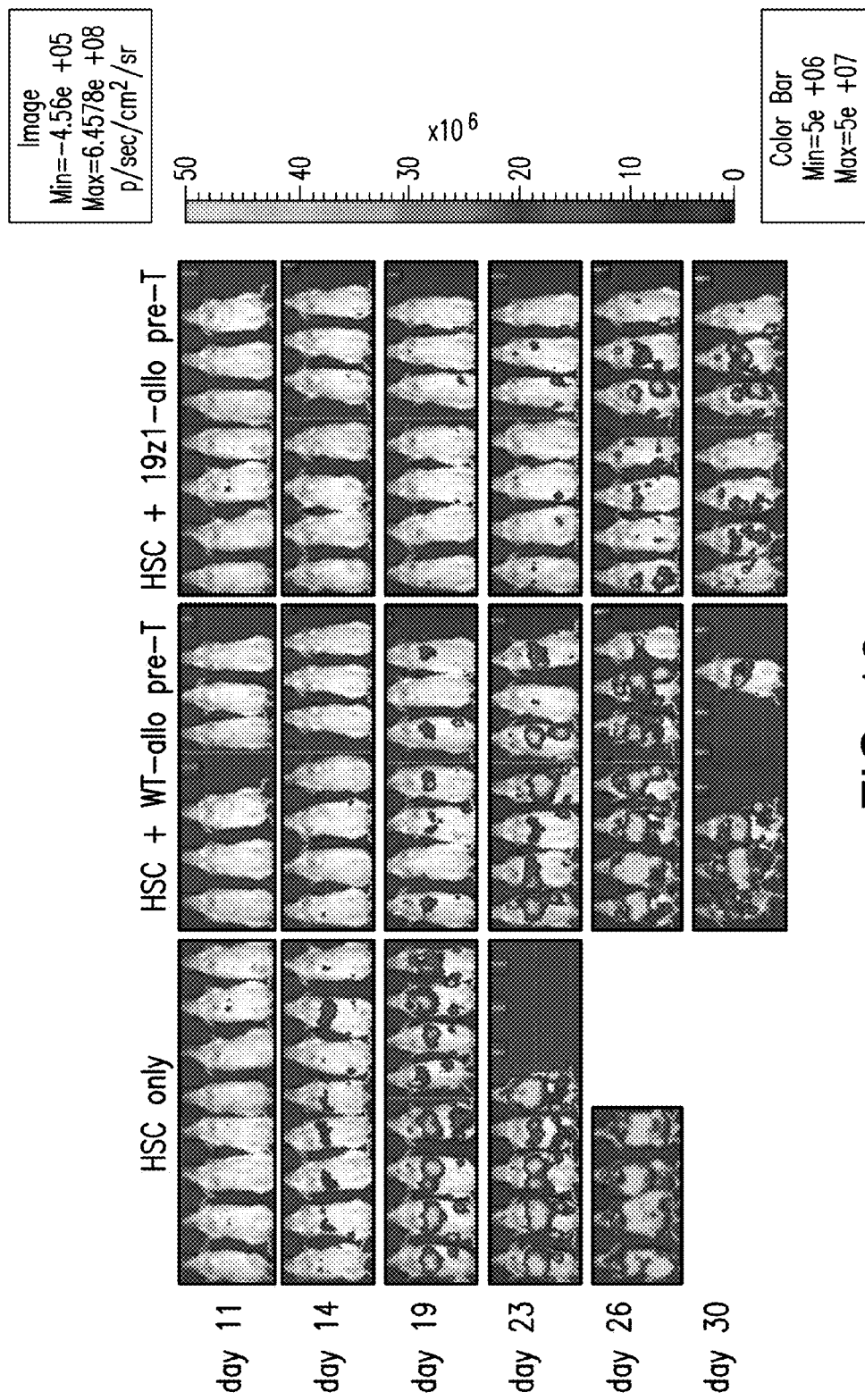
FIG. 16 is a series of photographs which depict a comparison of unmanipulated and genetically engineered cells.

Applicants challenged mice with A20-TGL-hCD19 to determine tumor growth by in vivo bioluminescence imaging. Lethally irradiated BALB/c recipients were transplanted with BALB/c hematopoietic stem cells only or received additional C57BL/6-derived T-cell precursors (unmanipulated or genetically engineered to express 19z1). All mice received $3.3 \times 10^5$ A20-TGL-hCD19 cells i.v. on day 0, and tumor growth was monitored by in vivo bioluminescence imaging. Mean SEM of bioluminescent signal intensity of 5 time points as well as pseudo-color images superimposed on conventional photographs on day 19 after HSCT are presented (n=7-8). As shown in FIG. 6d and FIG. 16, a significant increase in anti-tumor activity in recipients of 19z1-expressing T-cell precursors compared with recipients of untransduced T-cell precursors was found. FIG. 16 demonstrates that the anti-tumor activity of adoptively transferred allogeneic T-cell precursors can be genetically enhanced. Lethally irradiated BALB/c recipients were transplanted with BALB/c HSCs only or received additional C57BL/6-derived T-cell precursors (unmanipulated or genetically engineered to express 19z1) on day 0. All mice received 3.3×105 A20-TGL-hCD19 tumor cells i.v. on day. 0, and tumor growth was monitored by in vivo BLI. Pseudo-color images superimposed on conventional photographs on six time points after HSCT are presented (n=7-8).

Applicants' data therefore indicate that engineered T-cell precursors give rise to antigen-specific host-tolerant T-cells that can display cytotoxic activity upon stimulation with their specific antigen, traffic to the site of antigen expression in vivo and persist for at least six weeks after transfer. Importantly, no adverse effects were observed.

Example 7

Materials and Methods

A. Cells and cell lines. Single cell suspensions were prepared from spleen and thymus according to standard protocols. Harvest media consisted of RPMI-1640 supplemented with 10% heat inactivated fetal bovine serum (FBS), 100 U/ml penicillin, 100 µg/ml streptomycin and 2 mM L-glutamine. OP9-DL1, a bone marrow stromal cell line of (C57BL/6×C3H)F$_2$-op/op origin transduced with DL1, was described previously (see, e.g., Schmitt, T. M. & Zúñiga-Pflücker, J. C. Induction of T cell development from hematopoietic progenitor cells by delta-like-1 in vitro. Immunity 17, 749-756 (2002)). A20, a B cell lymphoma cell line of BALB/c origin, and Renca, a renal cell carcinoma cell line of BALB/c origin, were kindly provided by A. Houghton (Memorial Sloan Kettering Cancer Center). A20 was either used untransduced or retrovirally transduced, either to express a triple fusion protein consisting of Herpes simplex virus thymidine kinase, enhanced green fluorescent protein (eGFP) and firefly luciferase (TGL)[52], or to express human CD19 (transduction with SFG-hCD19 oncoretroviral vectors derived from gpg29 cells), or to express both TGL and hCD19. Renca was retrovirally transduced to express TGL, as described above. The construction of EL4-hCD19 and EL4-hPSMA has been described previously (see, e.g., Sadelain, M., Riviere, I. & Brentjens, R. Targeting tumours with genetically enhanced T lymphocytes. Nat Rev Cancer 3, 35-45 (2003)). Cell culture medium consisted of RPMI 1640 supplemented with 10% heat-inactivated FBS, 100 U/mL penicillin, 100 µg/mL streptomycin and 2 mM L-glutamine (for A20 and Renca), Dulbecco Modified Eagle's Medium (DMEM, Life Technologies) supplemented with 10% heat-inactivated FES, 100 U/mL penicillin, 100 µg/mL streptomycin and 2 mM L-glutamine (for EL4) and αMEM supplemented with 20% heat-inactivated FBS, 100 U/mL penicillin, 100 µg/mL streptomycin (for OP9-DL1). Cells were maintained at 37° C. in a humidified atmosphere containing 5% $CO_2$.

B. Mice and BM/HSC Transplantation. Female C57BL/6 (H-2$^b$), BALB/c (H-2$^d$), and C57BL/6 (CD45.1$^+$) mice were obtained from The Jackson Laboratory. Female Abb/B2m targeted mutation mice on a C57BL/6 background were purchased from Taconic. Mice used for experiments were 8-12 weeks old, unless otherwise specified. BM cells were removed aseptically from femurs and tibias. Donor BM was depleted for lineage marker-positive cells using the EasySep Hematopoietic Progenitor Cell Enrichment kit (Stem Cell Technologies) and used either for flow cytometric HSC isolation or for Lin$^-$ HSCT. BM cells were resuspended in DMEM and transplanted by tail vein injection ($1 \times 10^5$ cells in 0.2 mL total volume) into lethally irradiated recipients (BALE/c: 850 cGy, C57BL/6: 1100 cGy total body irradiation from a $^{137}$Cs source as a split dose with a 3 h interval between doses to reduce gastrointestinal toxicity). When purified HSCs were used for transplantation, $1 \times 10^3$ HSC in 0.2 mL DMEM were injected. In GVT experiments, animals received tumor cells intravenously in a separate injection on day 0. Mice were housed in sterilized micro-isolator cages and received normal chow and autoclaved hyper-chlorinated drinking water (pH 3.0). The Memorial Sloan-Kettering Cancer Center Institutional Animal Care and Use Committee approved all protocols involving experiments with animals.

C. Flow cytometry and cell sorting. Cells were washed in FACS buffer (PBS/0.5% BSA/0.1% sodium azide) and $10^6$ cells/mL were incubated for 15 m at 4° C. with CD16/CD32 FcR block. Subsequently, cells were incubated for 15 m at 4° C. with antibodies and washed twice with FACS buffer. The stained cells were resuspended in FACS buffer and analyzed on a LSR-II flow cytometer (Becton Dickinson) with DIVA software (Becton Dickinson). Data were analyzed with Flowjo (Treestar). For isolation of HSCs, BM cells from donor mice were obtained as described above. Cells were incubated with a mix of FITC conjugated lineage antibodies (antibodies to CD3, NK1.1, Gr-1, CD11b, CD19, CD4, CD8) and with Sca-1 and c-kit-specific antibodies. HSC (Lin$^-$Sca-1$^{hi}$c-kit$^{hi}$) were isolated using a MoFlo cell sorter (DakoCytomation). Sorted cells were ≥95% pure.

D. Assessment of GVHD, GVT, in vivo BLI. The severity of GVHD was assessed with a clinical GVHD scoring system as previously described (see, e.g., Cooke, et al., An experimental model of idiopathic pneumonia syndrome after bone marrow transplantation: I. The roles of minor H antigens and endotoxin, Blood 88, 3230-3239 (1996)). Briefly, ear tagged animals in coded cages were individually scored every week for five clinical parameters on a scale from zero to two: weight loss, posture, activity, fur and skin. A clinical GVHD index was generated by summation of the five criteria scores (zero-ten). Survival was monitored daily. Animals were sacrificed after HSCT for histopathological analysis of GVHD target organs (small bowel, large bowel, and liver). Organs were harvested, formalin-preserved, paraffin-embedded, sectioned and hematoxylin/eosin-stained. A semiquantitative score consisting of 19 to 22 different parameters associated with GVHD was calculated. In GVT experiments, bioluminescent signal intensity of tumor-bearing mice was determined twice weekly. 15 m after intraperitoneal injection of 3 mg/mouse 0-Luciferin (Xenogen), mice were anaesthetized and placed into the light tight chamber of an IVIS 200 bioluminescence imaging system (Xenogen). Grayscale photographic images of the mice were acquired first and then a low-level bioluminescent signal was recorded. Pseudo-color images showing the whole body distribution of bioluminescent signal intensity were superimposed on the grayscale photographs and total flux (photons/s) was determined for individual mice. The cause of death was confirmed by necropsy and histopathology.

E. Retroviral transduction and expansion of T cell precursors. T cell precursors were developed in vitro from C57BL/6 BM derived HSCs using the OP9-DL1 culture system, as described above. Lentiviral vectors were produced by tripartite transfection of 293T cells with pRRL-hPGKpr-19z1-WPRE, pCMVΔR8.92, and pUCMD.G. Vector supernatants were concentrated by ultra-centrifugation and 0.75-1.5×10$^8$ total TO used to transduce 5×10$^5$ T cell precursors (coculture day 4-6) over 2 days in 24-well tissue culture plates coated with 15 ug/ml retronectin and 10 ug/ml DL1$^{ext-IgG}$. Transduced cells were then expanded for an additional 14-21 days by OP9-DL1 coculture.

F. Reagents and Antibodies. Mouse-specific CD16/CD32 FcR block (clone 2.4G2) and all of the following fluorochrome or biotin-labeled monoclonal antibodies to mouse antigens were obtained from BD Biosciences: Ly9.1 (clone 3007), CD45.1 (clone A20), CD45 (clone 30-F11), H-2$^d$ (clone 34-2-12), CD3 (clone 145-2C11), CD4 (clone RM4-5), CD8a (clone 53-6.7), DX5 (clone DX5), CD11b (clone M1/70), CD11c (clone HL3), NK1.1 (clone PK136), Gr-1 (clone RB6-8C5), CD19 (clone 1D3), CD44 (clone IM7), CD25 (clone PC61), CD28 (clone 37.52), IFN-γ (clone XMG1.1), Lck (clone MOL171), mouse Vβ TCR screening panel, c-kit (clone 258), Sca-1 (clone D7), rat IgGl-κ (clone R3-34). The anti-idiotype monoclonal antibody 19e3-PE is specific for 19z1 and was a generous gift of the Gene Transfer Facility at Memorial Sloan Kettering Cancer Center. DL1$^{ext-IgG}$ was a generous gift of Irwin D. Bernstein, Fred Hutchinson Cancer Research Center. Retronectin was purchased from Takara Biomedicals. A fixation/permeabilization solution kit was also obtained from BD Biosciences. Diamidino-phenylindole (DAPI) (Molecular Probes) was used for dead cell discrimination. Brefeldin A was obtained from Calbiochem and recombinant mouse Flt3-ligand was purchased from R&D Systems, Inc. Recombinant human KGF was kindly provided by Amgen and recombinant human IL-7 was kindly provided by Cytheris.

G. Hematopoietic stem cell/OP9-DL1 cocultures. T lineage cells were generated in vitro as described previously with modifications (see, e.g., Schmitt, et al., Induction of T cell development from hematopoietic progenitor cells by delta-like-1 in vitro, Immunity 17, 749-756 (2002) and Zakrzewski, et al., Adoptive transfer of T-cell precursors enhances T-cell reconstitution after allogeneic hematopoietic stem cell transplantation, Nat Med 12, 1039-1047 (2006)). Briefly, HSC were isolated as described above and seeded on a 60-80% confluent monolayer of OP9-DL1 cells at densities ranging from 3-8×10$^4$ cells/well into six-well tissue culture plates. The tissue culture media was supplemented with 5 ng/mL IL-7 and 5-10 ng/mL Flt3-ligand. Every 4-5 days, cells were collected by forceful pipetting, filtered through a 70 μm nylon mesh and seeded into a new tissue culture vessel containing a monolayer of OP9-DL1 cells. Cells were maintained as predominantly DN2 and DN3 T-cell precursors from day 14 of coculture on until they were used for experiments (the latest at day 28).

I. Mixed Leukocyte Reactions. T-cells (seeded at a density of 1×10$^5$ T-cells/well) were cultured for five days with irradiated (2,000 cGy) BALB/c, C57BL/6 or CBA derived splenocytes as stimulators (2×10$^5$ cells/well) in a 96-well plate. $^3$H-Thymidine was added for the final 18 hours of culture. Cells were harvested with a Filtermate 196 harvester (Packard, Meridan, Conn.) and after addition of Microscint-20 scintillation fluid (Packard), counts per minute were measured with a Topcount NXT microplate scintillation counter (Packard). Counts are presented as stimulation index (counts in MLR/counts in spontaneous proliferation).

J. Intracellular cytokine staining. For unspecific stimulation, cells were incubated for 16 h in 24-well tissue culture plates coated with anti-CD3 (10 μg/mL) in the presence of soluble anti-CD28 (10 μg/mL). Brefeldin A (10 μg/mL) was added after one hour of incubation. For antigen-specific stimulation, cells were stimulated for 16 h with irradiated A20 or A20-TGL cells (20,000 cGy) in the presence of soluble anti-CD28 (10 μg/mL), at a ratio of 2:1, or with irradiated EL4-hCD19 or EL4-hPSMA (7,500 cGy), at a ratio of 5:1. Brefeldin A (10 μg/mL) was added after one hour. Following stimulation, cells were harvested, washed, and stained with fluorochrome-conjugated antibodies to surface antigens. Subsequently, cells were fixed and permeabilized with fixation/permeabilization solution kit reagents according to the manufacturer's instructions and stained with IFN-γ, Lck or rat IgGl-κ (isotypic control)-specific antibodies. Cells were analyzed by multicolor flow cytometry as described above.

K. Interferon-Gamma Enzyme-Linked Immunospot. ELISPOT assays measuring mouse IFN-γ were used to assess T-cell responses to stimulation with A20-TGL or EL4-TGL cells. Multiscreen-IP plates (Millipore) were coated with 100 μl anti-mouse IFN-γ monoclonal antibody (10 mg/mL; clone AN18, MabTech) in PBS, incubated overnight at 4° C., washed with RPMI/FCS to remove unbound antibody, and blocked with RPMI/FCS for 2 h at 37° C. T-cells were plated at a density of 5×10$^4$ CD8$^+$ T-cells per well and stimulated with irradiated A20-TGL or EL4-TGL cells (10$^4$ per well) in a final volume of 200 μl/well. After incubation at 37° C. for 20 h, plates were washed with PBS/0.05% Tween, and incubated with 100 μl per well biotinylated antibody to mouse IFN-γ (1 mg/mL; clone RA-6A-2, MabTech). Plates were incubated for an additional 2 h at 37° C. followed by spot development. Spots were counted with an Automated ELISpot Reader System with KS 4.3 software (Carl Zeiss MicroImaging Inc.).

L. Statistics. All results in this manuscript are based on two-sided test statistics. A P-value <0.05 was considered statistically significant. The Mann-Whitney U-statistic was used to compare flow cytbmetric data. In vivo data regarding survival, weight changes, and photon intensity determined by in vivo BLI were collected in studies assessing GVHD and GVT. For those studies, mice were randomly assigned to the treatment groups and the area under the curve (AUC) was used to summarize the weight and photon trajectory of each mouse under study. Not all the mice were followed for the full length of the study. The primary reason for censoring was death or sacrifice, and ignoring this type of informative censoring may result in a biased treatment comparison. To eliminate this bias, a test statistic was formed using the information up to the minimum follow up time for each cross treatment mouse pair. By eliminating the uneven censorship between mouse pairs in different groups, a test statistic can be constructed that has mean zero when the growth rates in the two groups are equal. The statistic is based on the average difference in the censored AUC curves between treatment groups. The log rank test statistic was used to compare survival curves between groups. For the analyses of the imaging studies, the P-values were generated from a permutation test, using the AUC and log rank test statistics. The application of the permutation procedure was due to the small number of animals in these studies.

REFERENCES

The following literature references are believed to be useful to an understanding of the inventive subject matter in the context of its place in the relevant art. Citation here is not to be construed as an assertion or admission that any reference cited is material to patentability of the inventive subject matter. Applicants will properly disclose information material to patentability in an Information Disclosure Statement.

1. Mackall, C. L. & Gress, R. E. Thymic aging and T-cell regeneration. Immunol Rev 160, 91-102 (1997).
2. Grunebaum, E., Sharfe, N. & Roifman, C. M. Human T cell immunodeficiency: when signal transduction goes wrong. Immunol Res 35, 117-126 (2006).
3. Fischer, A. et al. Naturally occurring primary deficiencies of the immune system. Annu Rev Immunol 15, 93-124 (1997).
4. Chinen, J., Finkelman, F. & Shearer, W. T. Advances in basic and clinical immunology. J Allergy Clin Immunol 118, 489-495 (2006).
5. Lehrnbecher, T., Foster, C., Vázquez, N., Mackall, C. L. & Chanock, S. J. Therapy-induced alterations in host defense in children receiving therapy for cancer. J Pediatr Hematol Oncol 19, 399-417 (1997).
6. Yarilin, A. A. et al. Late T cell deficiency in victims of the Chernobyl radiation accident: possible mechanisms of induction. Int J Radiat Biol 63, 519-528 (1993).
7. Appelbaum, F. R. Haematopoietic cell transplantation as immunotherapy. Nature 411, 385-389 (2001).
8. Joao, C. et al. Early lymphocyte recovery after autologous stem cell transplantation predicts superior survival in mantle-cell lymphoma. Bone Marrow Transplant 37, 865-871 (2006).
9. Leemhuis, T., Wells, S., Scheffold C., Edinger, M. & Negrin, H. S. A phase I trial of autologous cytokine-induced killer cells for the treatment of relapsed Hodgkin disease and non-Hodgkin lymphoma. Biol Blood Marrow Transplant 11, 181-187 (2005).
10. Gordan, L. N. et al. Correlation of early lymphocyte recovery and progression-free survival after autologous stem-cell transplant in patients with Hodgkin's and non-Hodgkin's Lymphoma Bone Marrow Transplant 31, 1009-1013 (2003).
11. Porrata, L. F. et al. Early lymphocyte recovery is a predictive factor for prolonged survival after autologous hematopoietic stem cell transplantation for acute myelogenous leukemia Leukemia 16, 1311-1318 (2002).
12. Porrata, L. F. et al. Early lymphocyte recovery post-autologous haematopoietic stem cell transplantation is associated with better survival in Hodgkin's disease. Br J Haematol 117, 629-633 (2002).
13. Porrata, L. F. et al. Early lymphocyte recovery predicts superior survival after autologous hematopoietic stem cell transplantation in multiple myeloma or non-Hodgkin lymphoma. Blood 98, 579-585 (2001).
14. Porrata, L. F., Ingle, J. N., Litzow, M. R., Geyer, S. & Markovic, S. N. Prolonged survival associated with early lymphocyte recovery after autologous hematopoietic stem cell transplantation for patients with metastatic breast cancer. Bone Marrow Transplant 28, 865-871 (2001).
15. Kolb, H. J. et al. Graft-versus-leukemia effect of donor lymphocyte transfusions in marrow grafted patients. European Group for Blood and Marrow Transplantation Working Party Chronic Leukemia. Blood 86, 2041-2050 (1995).
16. Gottschalk, S., Heslop, H. E. & Rooney, C. M. Adoptive immunotherapy for EBV-associated malignancies. Leuk Lymphoma 46, 1-10 (2005).
17. Gottschalk, S., Heslop, H. E. & Rooney, C. M. Treatment of Epstein-Barr virus-associated malignancies with specific T cells. Adv Cancer Res 84, 175-201 (2002).
18. Rooney, C. M. et al. Infusion of cytotoxic T cells for the prevention and treatment of Epstein-Barr virus-induced lymphoma in allogeneic transplant recipients. Blood 92, 1549-1555 (1998).
19. Rooney, C. M. et al. Use of gene-modified virus-specific T lymphocytes to control Epstein-Barr-virus-related lymphoproliferation. Lancet 345, 9-13 (1995).
20. Heslop, H. E., Brenner, M. K. & Rooney, C. M. Donor T cells to treat EBV-associated lymphom. N Engl J Med 331, 679-680 (1994).
21. Yotnda, P. et al. Cytotoxic T cell response against the chimeric p210 BCR-ABL protein in patients with chronic myelogenous leukemia. J Clin Invest 101, 2290-2296 (1998).
22: Luznik, L. et al. Successful therapy of metastatic cancer using tumor vaccines in mixed allogeneic bone marrow chimeras. Blood 101, 1645-1652 (2003).
23. Schmitt, T. M. & Zúñiga-Pflücker, J. C. Induction of T cell development from hematopoietic progenitor cells by delta-like-1 in vitro. Immunity 17, 749-756 (2002).
24. Ohishi, K., Varnum-Finney, B. & Bernstein, I. D. Delta-1 enhances marrow and thymus repopulating ability of human CD34(+)CD38(−)cord blood cells. J Clin Invest 110, 1165-1174 (2002).
25. De Smedt, M., Hoebeke, I. & Plum, J. Human bone marrow CD34+ progenitor cells mature to T cells on OP9-DL1 stromal cell line without thymus microenvironment. Blood Cells Mol Dis 33, 227-232 (2004).
26. La Motte-Mohs, R. N., Herer, E. & Zúñiga-Pflücker, J. C. Induction of T cell development from human cord blood hematopoietic stem cells by Delta-like 1 in vitro. Blood 105, 1431-1439 (2005).

27. Zakrzewski, J. L. et al. Adoptive transfer of T-cell precursors enhances T-cell reconstitution after allogeneic hematopoietic stem cell transplantation. Nat Med 12, 1039-1047 (2006).

28. Dallas, M. H., Varnum-Finney, B., Martin, P. J. & Bernstein, I. D. Enhanced T-cell reconstitution by hematopoietic progenitors expanded ex vivo using the Notch ligand Delta1. Blood 109, 3579-3587 (2007).

29. Schmitt, T. M. et al. Induction of T cell development and establishment of T cell competence from embryonic stem cells differentiated in vitro. Nat Immunol 5, 410-417 (2004).

30. Cooke, K. R. et al. An experimental model of idiopathic pneumonia syndrome after bone marrow transplantation: I. The roles of minor H antigens and endotoxin. Blood 88, 3230-3239 (1996).

31. Hill, G. R. et al. Total body irradiation and acute graft-versus-host disease: the role of gastrointestinal damage and inflammatory cytokines. Blood 90, 3204-3213 (1997).

32. Acha-Orbea, H. & MacDonald, H. R. Superantigens of mouse mammary tumor virus. Annu Rev Immunol 13, 459-486 (1995).

33. Abe, R., Kanagawa, O., Sheard, M. A., Malissen, B. & Foo-Phillips, M. Characterization of a new minor lymphocyte stimulatory system. I. Cluster of self antigens recognized by "I-E-reactive" V beta s, V beta 5, V beta 11, and V beta 12 T cell receptors for antigen. J Immunol 147, 739-749 (1991).

34. Woodland, D., Happ, M. P., Bill, J. & Palmer, E. Requirement for cotolerogenic gene products in the clonal deletion of I-E reactive T cells. Science 247, 964-967 (1990).

35. Bill, J., Kanagawa, O., Woodland, D. L. & Palmer, E. The MHC molecule I-E is necessary but not sufficient for the clonal deletion of V beta 11-bearing T cells. J Exp Med 169, 1405-1419 (1989).

36. Vacchio, M. S. & Hodes, R. J. Selective decreases in T cell receptor V beta expression. Decreased expression of specific V beta families is associated with expression of multiple MHC and non-MHC gene products. J Exp Med 170, 1335-1346 (1989).

37: Anderson, G. & Jenkinson, E. J. Lymphostromal interactions in thymic development and function. *Nat Rev Immunol* 1, 31-40 (2001).

38. Kessels, H. W., Wolkers, M. C., van den Boom, M. D., van der Valk, M. A. & Schumacher, T. N. Immunotherapy through TCR gene transfer. Nat Immunol 2, 957-961 (2001).

39. Brentjens, R. J. et al. Eradication of systemic B-cell tumors by genetically targeted human T lymphocytes co-stimulated by CD80 and interleukin-15. Nat Med 9, 279-286 (2003).

40. Sadelain, M., Riviere, I. & Brentjens, R. Targeting tumours with genetically enhanced T lymphocytes. Nat Rev Cancer 3, 35-45 (2003).

41. Morgan, R. A. et al. Cancer regression in patients after transfer of genetically engineered lymphocytes. Science 314, 126-129 (2006).

42. Zhao, Y. et al. Extrathymic generation of tumor-specific T cells from genetically engineered human hematopoietic stem cells via Notch signaling. Cancer Res 67, 2425-2429 (2007).

43. Bousso, P., Bhakta, N. R., Lewis, R. S. & Robey, E. Dynamics of thymocyte-stromal cell interactions visualized by two-photonmicroscopy Science 296, 1876-1880 (2002).

44. Ernst, B. B., Surh, C. D. & Sprent, J. Bone marrow-derived cells fail to induce positive selection in thymus reaggregation cultures J Exp Med 183, 1235-1240 (1996).

45. Bix, M. & Raulet, D. Inefficient positive selection of T cells directed by haematopoietic cells. Nature 359, 330-333 (1992).

46. Wu, L., Li, C. L. & Shortman, K. Thymic dendritic cell precursors: relationship to the T lymphocyte lineage and phenotype of the dendritic cell progeny. J Exp Med 184, 903-911 (1996).

47. Chen, H. Q. et al. T/NK bipotent progenitors in the thymus retain the potential to generate dendritic cell. J Immunol 171, 3401-3406 (2003).

48. Liggins, A. P., Guinn, B. A. & Banham, A. H. Identification of lymphoma-associated antigens using SEREX. Methods Mol Med 115, 109-128 (2005).

49. Greiner, J. et al. Expression of tumor-associated antigens in acute myeloid leukemia: Implications for specific immunotherapeutic approache. Blood 108, 4109-4117 (2006).

50. Cohen, J. I. Benign and malignant Epstein-Barr virus-associated B-cell lymphoproliferative diseases. Semin Hematol 40, 116-123 (2003).

51. Yang, L., Qin, X. F., Baltimore, D. & van Parijs, L. Generation of functional antigen-specific T cells in defined genetic backgrounds by retrovirus-mediated expression of TCR cDNAs in hematopoietic precursor cells. Proc Natl Acad Sci USA 99, 6204-6209 (2002).

52. June, C. H. Adoptive T cell therapy for cancer in the clinic. J Clin Invest 117, 1466-1476 (2007).

53. Terwey, T. H. et al. CCR2 is required for CD8-induced graft-versus-host disease. Blood 106, 3322-3330 (2005).

54. May, C. et al. Therapeutic haemoglobin synthesis in β-thalassaemic mice expressing lentivirus-encoded human β-globin. Nature 406, 82-86 (2000).

55. Vardi, Y., Ying, Z. & Zhang, C. H. Two-sample tests for growth curves under dependent right censoring Biometrika 88, 949-960 (2001).

The inventive subject matter being thus described, it will be obvious that the same may be modified or varied in many ways. Such modifications and variations are not to be regarded as a departure from the spirit and scope of the inventive subject matter and all such modifications and variations are intended to be included within the scope of the following claims.

What is claimed is:

1. A method for treating a human T-cell deficiency in a subject in need thereof, comprising administering to said subject a composition comprising double negative (DN) T-cell precursors from an allogeneic donor, wherein said DN T-cell precursors consist essentially of:

cells having a DN2 ($CD44^+CD25^+$) phenotype or phenotype of an equivalent human DN precursor thereof, cells having a DN3 ($CD44^-CD25^+$) phenotype or phenotype of an equivalent human DN precursor thereof, or cells having a DN2 ($CD44^+CD25^+$) phenotype or a phenotype of an equivalent human DN precursor thereof and cells having a DN3 ($CD44^-CD25^+$) phenotype or phenotype of an equivalent human DN precursor thereof, wherein the major histocompatibility complex (MHC) of said allogeneic donor is not matched to the MHC of said subject, wherein said DN T-cell precursors comprise a nucleic acid sequence which encodes for a chimeric antigen receptor.

2. The method of claim 1, wherein said chimeric antigen receptor is specific for an antigen of a target cancer cell.

3. The method of claim 2, wherein said antigen is CD19.

4. The method of claim 3, wherein said chimeric antigen receptor is 19z1.

5. The method of claim 2, wherein said DN T-cell precursors express one or more proteins selected from the group consisting of costimulatory molecules CD26, CD28, CD40, CD80, CD86, CD134, CD154, and combinations thereof.

6. The method of claim 1, wherein said DN T-cell precursors are generated by ex vivo culturing of hematopoietic stem cells from the allogeneic donor.

7. The method of claim 6, wherein said DN T-cell precursors are generated by ex vivo culturing said hematopoietic stem cells on a bone marrow derived stromal cell line expressing the Notch ligand Delta-like 1.

8. The method of claim 1, wherein said DN T-cell precursors consist essentially of the cells having the DN2 ($CD44^+CD25^+$) phenotype or phenotype of the equivalent human DN precursor thereof and the cells having the DN3($CD44^-CD25^+$) phenotype or phenotype of the equivalent DN precursor thereof.

9. The method of claim 1, wherein said DN T-cell precursors are derived from lineage $lin^-Sca\text{-}1^{+c\text{-}kithi}$ or a human equivalent $CD34^+$lineage.

10. The method of claim 1, wherein said T-cell deficiency is selected from the group consisting of acute lymphoblastic leukemia, acute lymphocytic leukemia, acute myelogenous leukemia, aplastic anemia, chronic myelogenous leukemia, desmoplastic small round cell tumor, Ewing's sarcoma, Hodgkin's disease, multiple myeloma, myelodysplasia, Non-Hodgkin's lymphoma, paroxysmal nocturnal hemoglobinuria, radiation poisoning, chronic lymphocytic leukemia, AL amyloidosis, essential thrombocytosis, polycythemia vera, severe aplastic anemia, neuroblastoma, breast tumors, ovarian tumors, renal cell carcinoma, autoimmune disorders, such as systemic sclerosis, osteopetrosis, inherited metabolic disorders, juvenile chronic arthritis, adrenoleukodystrophy, amegakaryocytic thrombocytopenia, sickle cell disease, severe congenital immunodeficiency, Griscelli syndrome type II, Hurler syndrome, Kostmann syndrome, Krabbe disease, metachromatic leukodystrophy, thalassemia, hemophagocytic lymphohistiocytosis, and Wiskott-Aldrich syndrome.

* * * * *